US006485904B1

(12) United States Patent
Rosey et al.

(10) Patent No.: US 6,485,904 B1
(45) Date of Patent: Nov. 26, 2002

(54) DNA ENCODING A PLASMINOGEN ACTIVATING PROTEIN

(75) Inventors: Everett L. Rosey, Preston; Robert J. Yancey, Jr., Salem, both of CT (US); James A. Leigh, Newbury (GB)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/078,091

(22) Filed: May 13, 1998

Related U.S. Application Data
(60) Provisional application No. 60/050,565, filed on Jun. 23, 1997.

(51) Int. Cl.$^7$ .................................................. C12Q 1/68
(52) U.S. Cl. ...................... 435/6; 435/69.3; 435/252.3; 435/320.1; 435/325; 514/44; 536/23.7
(58) Field of Search ............................... 536/23.1, 23.7; 514/44; 435/6, 69.3, 252.3, 320.1, 325

(56) References Cited

U.S. PATENT DOCUMENTS

| 5,198,214 A | | 3/1993 | Stolle et al. |
| 5,234,684 A | | 8/1993 | Sordillo et al. |
| 5,302,527 A | * | 4/1994 | Birkett et al. |
| 5,840,315 A | * | 11/1998 | Leigh |
| 5,908,629 A | * | 6/1999 | Michel et al. |

OTHER PUBLICATIONS

Plotkin et al ( *Vaccines* W B Saunders Co. Philadelphia p. 571), 1988.*
Smith, Elem.Mol.Neurobio. 2nd ed., p.74–82, 1996.*
Lazar et al, Mol.Cell Bio., 8:1247–1252, 1988.*
Burgess et al, J.Cell Bio. 111:2129–2138, 1990.*
Boehringer Mannheim Biochemicals 1991 Catalog, p.557, 1991.*
Leigh, J. A., 1993, Activation of bovine plasminogen by *Streptococcus uberis*, FEMS Microbiol. Letts. 114:67–72.
Leigh, J. A., 1994, Purification of a plasminogen activator from *Streptococcus uberis*, FEMS Microbiol. Letts. 118:153–158.
Malke, H. and Ferretti, J. J., 1984, Streptokinase: cloning, expression, and excretion by *Escherichia coli*, Proc. Natl. Acad. Sci. USA 81:3557–3561.
Tillet, W S. & Garner, R. L., 1933, The Fibrinolytic Activity of Hemolytic Streptococci, J. Exp. Med. 58:485–502.
Ling et al., 1967, J. Biol. Chem. 242(7):1419–1425, "Isolation and characterization of bovine plasminogen activator from a human plasminogen–streptokinase mixture" Abstract 66:72476v.
Yamamoto et al., 1976, Nippon Ketsueki Gakkai Zasshi 39(2):158–162, "Studies on a plasminogen activating system in human milk. III. Mechanism of formation of streptokinase–induced plasminogen activator" Abstract 85:75661e.

* cited by examiner

*Primary Examiner*—Mark Navarro
(74) *Attorney, Agent, or Firm*—Scully, Scott, Murphy & Presser

(57) ABSTRACT

The present invention provides polynucleotide molecules comprising nucleotide sequences encoding plasminogen activating (PauA) proteins from *Streptococcus uberis*, and substantially homologous polypeptides, peptide fragments, and fusion proteins thereof. The present invention further provides compositions and methods for recombinantly expressing the PauA proteins, substantially homologous polypeptides, peptide fragments and fusion proteins encoded by the polynucleotide molecules of the present invention. The present invention further provides a vaccine for protecting a member of a mammalian species against mastitis, comprising a PauA protein, substantially homologous polypeptide, peptide fragment, fusion protein, or polynucleotide molecule of the present invention.

54 Claims, 6 Drawing Sheets

Figure 2:
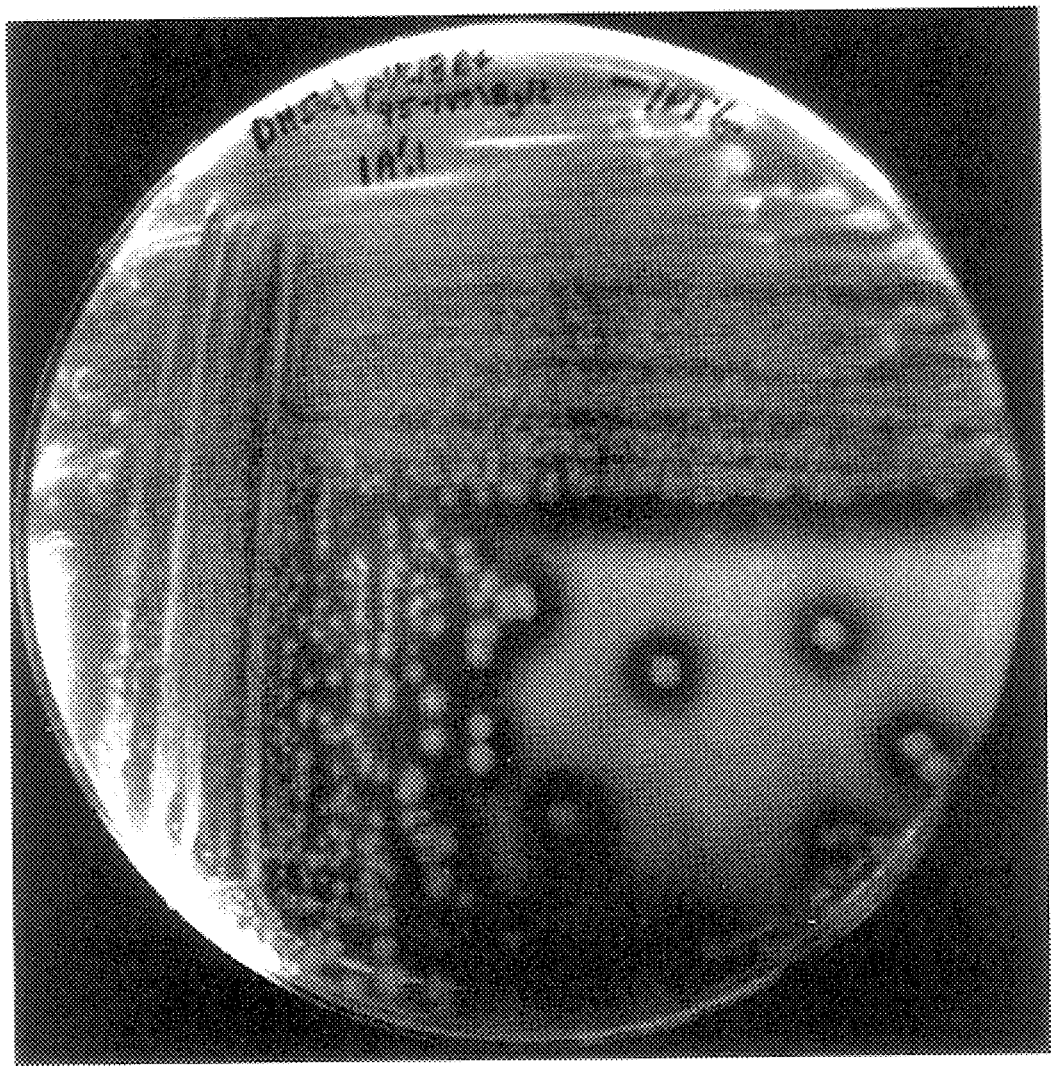

| Oligonucleotide<br>Name | Strand<br>Sense | SEQ<br>ID No. | Sequence (5'-3')<br>1.........10.........20.........30.........40.........50 |
|---|---|---|---|
| AP-1 | − | 13 | ATCATATAGTCAGGGTAGAG |
| RA-9 | + | 14 | cgggtaccGWTATATTGATCCWGATGARAA |
| ER-35 | − | 15 | gggatccTTTTGATCAATWGGATAATCWGGATA |
| ER-36 | + | 16 | ggggatccTTYTGRTCRATWGGRTARTCWGGRTA |
| ER-37 | − | 17 | GTTACAAAGGCCGAGTTGTTAGAC |
| ER-39 | − | 18 | GATTGGCAAATAAAAGCCGTCGATC |
| ER-40 | − | 19 | CTTCAAGTGATACGGATTCCTC |
| ER-41 | + | 20 | GGGGAATTCCACCCACTACC |
| ER-42 | + | 21 | GACGAGTTTCGAAAATTGCAGAAG |
| ER-43 | + | 22 | gggctgcagtcatATGAAAAATGGTTTTTAATATTAATGCTTTTGGG |
| ER-44 | + | 23 | gggctgcagtcatatgATAACCGGTTATGATTCCGACTACG |
| ER-45 | − | 24 | GAGATTCCTCTCtAGATATCA |
| ER-46 | + | 25 | gggctgcagATCCGTTAAAAAATGACATTAATAT |

FIG. 1

DNA ENCODING A PLASMINOGEN ACTIVATING PROTEIN

This application claims priority under 35 U.S.C. §119(e) from U.S. provisional application Ser. No. 60/050,565, filed Jun. 23, 1997.

1. FIELD OF THE INVENTION

The present invention is in the field of animal health, and is directed to vaccine compositions and diagnostics for disease. More particularly, the present invention relates to vaccines against mastitis in mammals, and polynucleotide molecules having nucleotide sequences encoding plasminogen activating proteins useful in the production of said vaccines.

2. BACKGROUND OF THE INVENTION

Bovine mastitis causes significant loss of milk production in dairy cattle, resulting in severe economic impact on the dairy industry. Mastitis may be caused by one or more types of bacterial pathogens. Infection by Streptococcus is estimated to account for approximately 30% of all clinical cases of bovine mastitis. Infection by S. uberis, specifically, is estimated to account for approximately 20% of all clinical cases of bovine mastitis.

Conventional methods for the prevention and treatment of mastitis in animals include the use of sanitary milking techniques and the administration of chemical antibiotics. The use of antibiotics, however, is limited by the fact that milk containing antibiotic residues is often not considered safe for human consumption and must be discarded. Specific approaches to the treatment or prevention of mastitis in animals include that of U.S. Pat. No. 5,198,214 to Stolle et al., which describes the use of polyvalent anti-mastitis vaccines comprising inactivated mastitis-causing pathogens cultivated from the milk of infected animals. In addition, U.S. Pat. No. 5,234,684 to Sordillo et al. describes a method of treating or preventing mastitis in cows, comprising administering bovine interferon gamma to the animals.

The ability of Streptococcus spp. to infect the lactating mammary gland is dependent on the bacteria's ability to grow in the secretion and avoid phagocytosis by bovine neutrophils (Leigh et al., 1990, Res. Vet. Sci. 49: 85–87). The majority of nitrogen in bovine milk is present in the form of protein (Aston, 1975, Austral. J. Dairy Tech. 30: 55–59) and, in the absence of proteolysis, growth of Streptococci in milk is limited by the lack of free amino acids. This is highlighted by the dependence of the lactic streptococci on extracellular, caseinolytic proteinases for growth in milk (Mills and Thomas, 1981, N. Zeal. J. Dairy Sci. Tech. 15: 43–55). In addition, the ability of bacteria to grow in milk is enhanced by the presence of the caseinolytic enzyme, plasmin (Marshall and Bramley, 1984, J. Dairy Res. 51:17–22), which breaks down milk proteins into free amino acids.

Bovine milk contains plasminogen that is normally proteolytically inactive, but which can be converted to proteolytically active plasmin by the action of a plasminogen activator. It has been demonstrated that mastitis-causing strains of Streptococcus, such as, e.g., S. uberis, produce a plasminogen activator capable of converting bovine plasminogen to plasmin. The activity of this plasminogen activator results in the break-down of milk protein to release free amino acids that, in turn, support the growth of the bacteria in the mammary gland. From this observation, it has been proposed that induction of an immune-based response, e.g., the production of neutralizing antibodies, against the plasminogen activator of Streptococcus, might serve to protect animals against mastitis. International Patent Publication WO 93/14209, which is incorporated herein by reference, demonstrates the purification of a plasminogen activator (designated therein as a "streptokinase") from culture filtrates of S. uberis, and further teaches anti-mastitis vaccine compositions based on such plasminogen activators from Streptococcus spp.

The isolation of a polynucleotide molecule having a nucleotide sequence encoding a plasminogen activator such as that, e.g., from Streptococcus, would greatly facilitate the preparation of anti-mastitis vaccines.

3. SUMMARY OF THE INVENTION

The present invention provides an isolated polynucleotide molecule comprising a nucleotide sequence encoding a biologically active plasminogen activator protein (designated herein as a "PauA protein," previously designated as "PA" or "streptokinase"). In a preferred embodiment, the PauA protein is from a bacterium, such as, e.g., Streptococcus, that causes or contributes to mastitis in a member of a mammalian species. In a more preferred embodiment, the species of Streptococcus is S. uberis or S. dysgalactiae.

In a preferred embodiment, the isolated polynucleotide molecule of the present invention comprises a nucleotide sequence encoding an amino acid sequence that is the same as the amino acid sequence from about amino acid position 26 (Ile) to about amino acid position 286 (Pro) of SEQ ID NO:2 or SEQ ID NO:4. In a non-limiting embodiment, such polynucleotide molecule comprises the nucleotide sequence from about nucleotide position 195 to about nucleotide position 977 of SEQ ID NO:1, or from about nucleotide position 196 to about nucleotide position 978 of SEQ ID NO:3, respectively.

In a further preferred embodiment, the isolated polynucleotide molecule of the present invention comprises a nucleotide sequence encoding an amino acid sequence comprising the amino acid sequence from about amino acid position 1 (Met) to about amino acid position 286 (Pro) of SEQ ID NO:2 or SEQ ID NO:4. In a non-limiting embodiment, such polynucleotide molecule comprises the nucleotide sequence from about nucleotide position 120 to about nucleotide position 980 of SEQ ID NO:1, or from about nucleotide position 121 to about nucleotide position 981 of SEQ ID NO:3, respectively. In a further non-limiting embodiment, the polynucleotide molecule of the present invention comprises the nucleotide sequence of SEQ ID NO:1, or the nucleotide sequence of SEQ ID NO:3, respectively.

The present invention further provides a polynucleotide molecule that is substantially homologous to the polynucleotide molecule of the present invention encoding a PauA protein.

The present invention further provides a polynucleotide molecule comprising a nucleotide sequence that encodes a polypeptide that is substantially homologous to a PauA protein encoded by a polynucleotide molecule of the present invention.

The present invention further provides a polynucleotide molecule consisting of a nucleotide sequence encoding a peptide fragment of a PauA protein or substantially homologous polypeptide of the present invention. In a specific though non-limiting embodiment, the present invention provides a polynucleotide molecule consisting of a nucleotide sequence encoding a peptide fragment consisting of a subsequence of amino acids from SEQ ID NO:2 or SEQ ID NO:4 selected from the group consisting of amino acids at positions of about 28 to about 286, about 104 to about 286, about 172 to about 286, about 28 to about 170, about 104 to about 170, about 104 to about 208, about 172 to about 208, about 28 to about 103, about 28 to about 208, and about 149 to about 286.

The present invention further provides a polynucleotide molecule comprising a nucleotide sequence that encodes a fusion protein comprising a PauA protein, substantially homologous polypeptide, or peptide fragment of the present invention joined to a carrier or fusion partner.

The present invention further provides oligonucleotide molecules that are useful as primers in amplification techniques, and as diagnostic probes in differential disease diagnosis. In a non-limiting embodiment, an oligonucleotide molecule of the present invention consists of a nucleotide sequence selected from the group consisting of SEQ ID NOS:13–27 and the complements of said sequences. In a further non-limiting embodiment, an oligonucleotide molecule of the present invention comprises a nucleotide sequence selected from the group consisting of SEQ ID NOS:13–27 and the complements of said sequences.

The present invention further provides compositions and methods for the recombinant expression of a polynucleotide molecule of the present invention, including recombinant cloning vectors and recombinant expression vectors comprising the polynucleotide molecule, and host cell lines transformed with any of said vectors.

The present invention further provides a recombinantly-expressed PauA protein, substantially homologous polypeptide, peptide fragment, or fusion protein encoded by a polynucleotide molecule of the present invention.

The present invention further provides analogs and derivatives of a PauA protein, substantially homologous polypeptide, peptide fragment or fusion protein of the present invention.

The present invention further provides a vaccine for protecting a member of a mammalian species against mastitis, comprising an immunologically effective amount of a PauA protein, substantially homologous polypeptide, peptide fragment, fusion protein, analog, derivative, or polynucleotide molecule of the present invention that is capable of inducing a protective response against mastitis in the mammal, and a veterinarily acceptable carrier. The vaccine can optionally comprise an adjuvant or other immunomodulatory component.

In a non-limiting embodiment, the vaccine of the present invention is a combination vaccine for protecting a member of a mammalian species against mastitis and, optionally, one or more other diseases or pathological conditions that can afflict the mammal, which combination vaccine comprises an immunologically effective amount of a first component comprising a PauA protein, substantially homologous polypeptide, peptide fragment, fusion protein, analog, derivative, or polynucleotide molecule of the present invention that is capable of inducing a protective response against mastitis in the mammal; an immunologically effective amount of a second component comprising an antigen capable of inducing a protective response against a disease or pathological condition that can afflict the mammal; and a veterinarily acceptable carrier.

The present invention further provides a method of preparing a vaccine for protecting a member of a mammalian species against mastitis, comprising combining an immunologically effective amount of a PauA protein, substantially homologous polypeptide, peptide fragment, fusion protein, analog, derivative, or polynucleotide molecule of the present invention that is capable of inducing a protective response against mastitis in the mammal, with a veterinarily acceptable carrier.

The present invention further provides a method of vaccinating a member of a mammalian species against mastitis, comprising administering the vaccine of the present invention to the mammal.

The present invention further provides antibodies that specifically bind to a PauA protein, substantially homologous polypeptide, peptide fragment, fusion protein, analog, or derivative of the present invention.

The present invention further provides vaccine kits and diagnostic kits.

4. BRIEF DESCRIPTION OF THE DRAWINGS

FIG. 1. Oligomeric probes (SEQ ID NOs: 13–25) designed based on peptide fragments from the PauA protein from S. uberis strain c216. Nucleotides in lower case do not match the chromosomal DNA sequence.

FIG. 2. Isolate of E. coli strain DH5α transformed with the pauA gene from S. uberis strain 95–140, cultured on a skim milk agarose plate further containing bovine plasminogen. Zones of clearing result from activation of plasminogen to plasmin and the subsequent breakdown of milk proteins.

Figure 3:
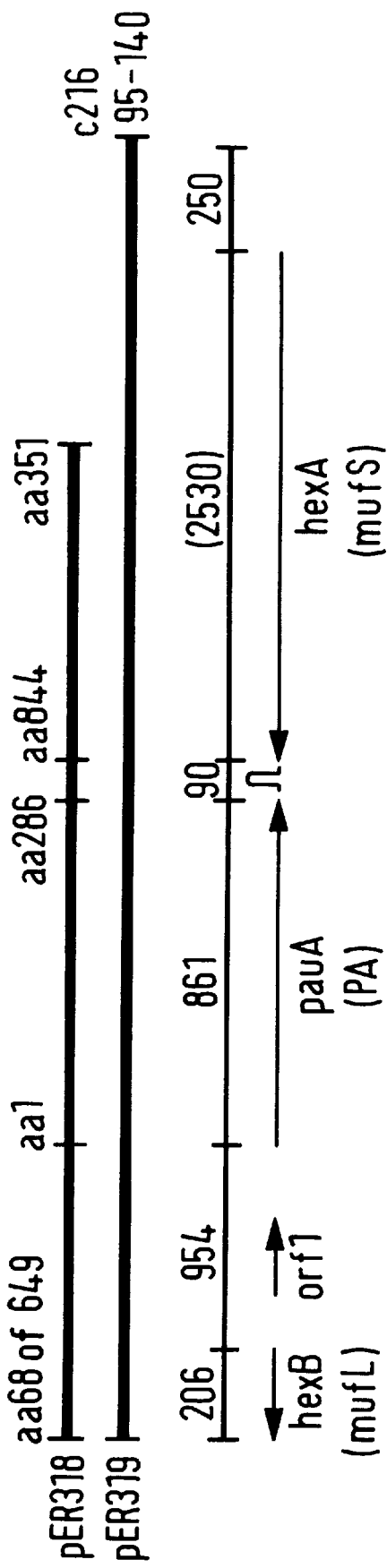

FIG. 3. pER318 and pER319 showing cloned pauA inserts with flanking HexA and HexB genes.

Figure 4:
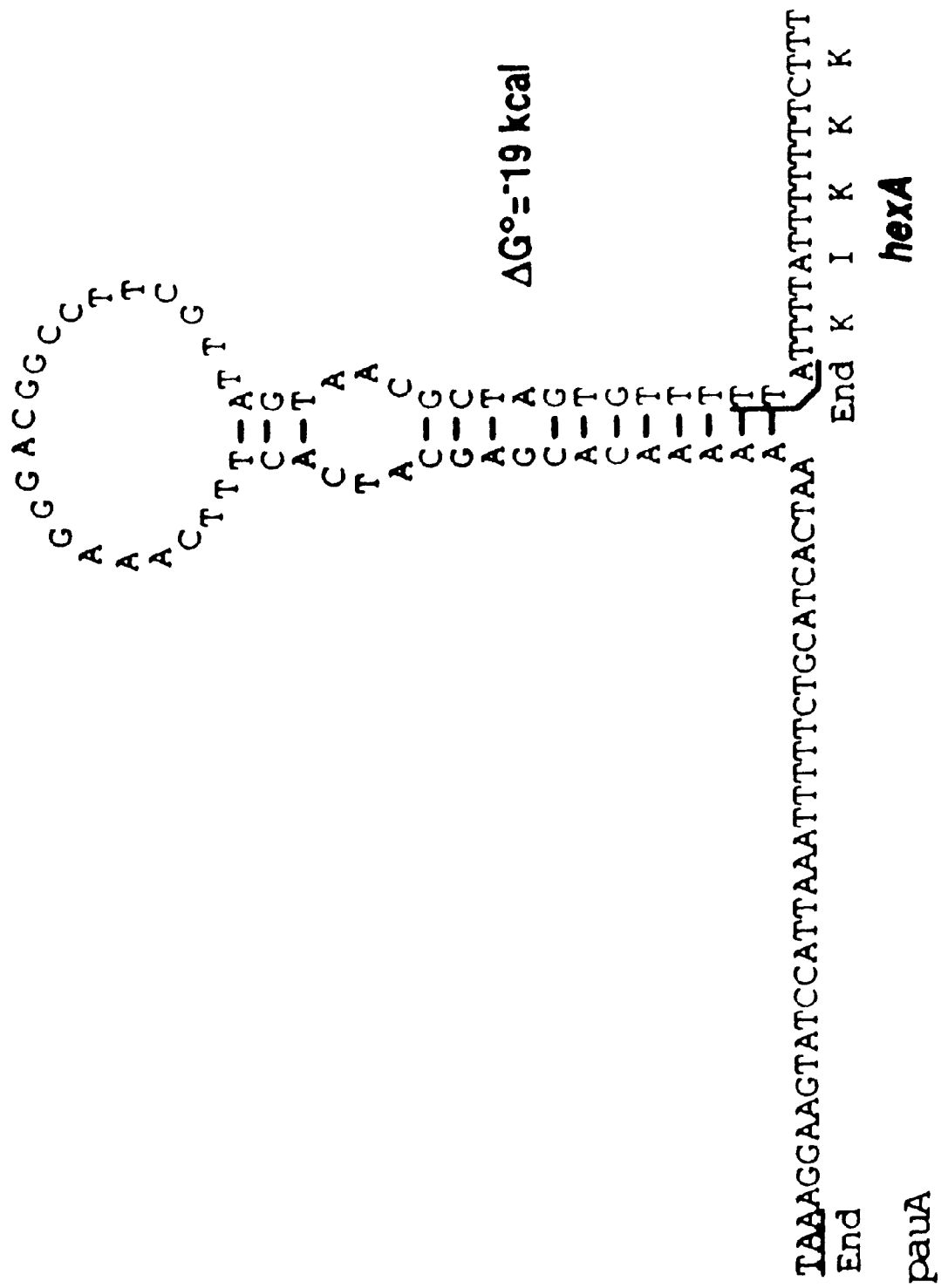

FIG. 4. Bi-directional terminator sequence in S. uberis strain c216, adjacent to ORF of pauA gene, at nts 978 to 1,088 of SEQ ID NO:1. The stop codon of the pauA ORF is underlined.

Figure 5:
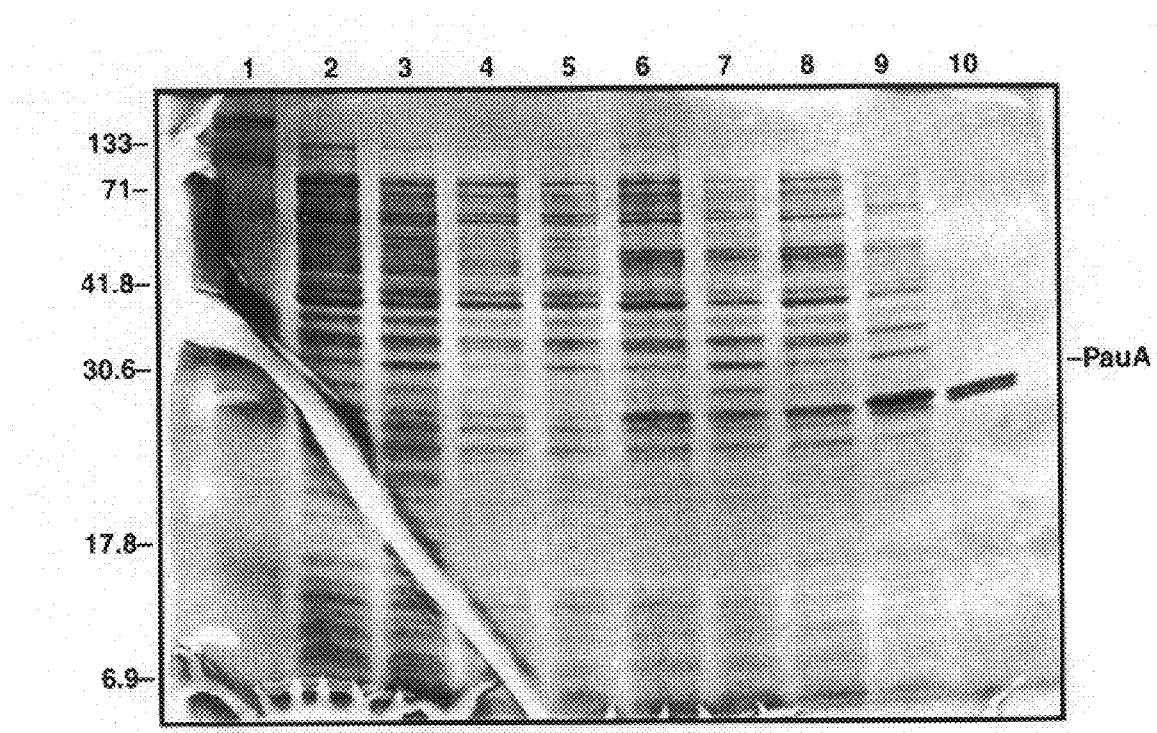

FIG. 5. Pre-induced and induced whole cell pellet lysate samples separated on SDS-PAGE and stained with Coomassie brilliant blue. Lane 1=molecular weight markers (RAINBOW Kaleidoscope pre-stained standards, Biorad Laboratories); 2=pre-induced strain Pz326 (containing plasmid pER326, with signal sequence); 3=post-induced strain Pz326; 4=pre-induced strain Pz328 (containing plasmid pER328, without signal sequence); 5=post-induced strain Pz328; 6=pre-induced strain Pz330 (containing plasmid pER330, with signal sequence); 7=post-induced strain Pz330; 8=pre-induced strain Pz332 (containing plasmid pER332, without signal sequence); 9=post-induced strain Pz332; 10=purified PauA protein from S. uberis strain 95–140.

Figure 6:
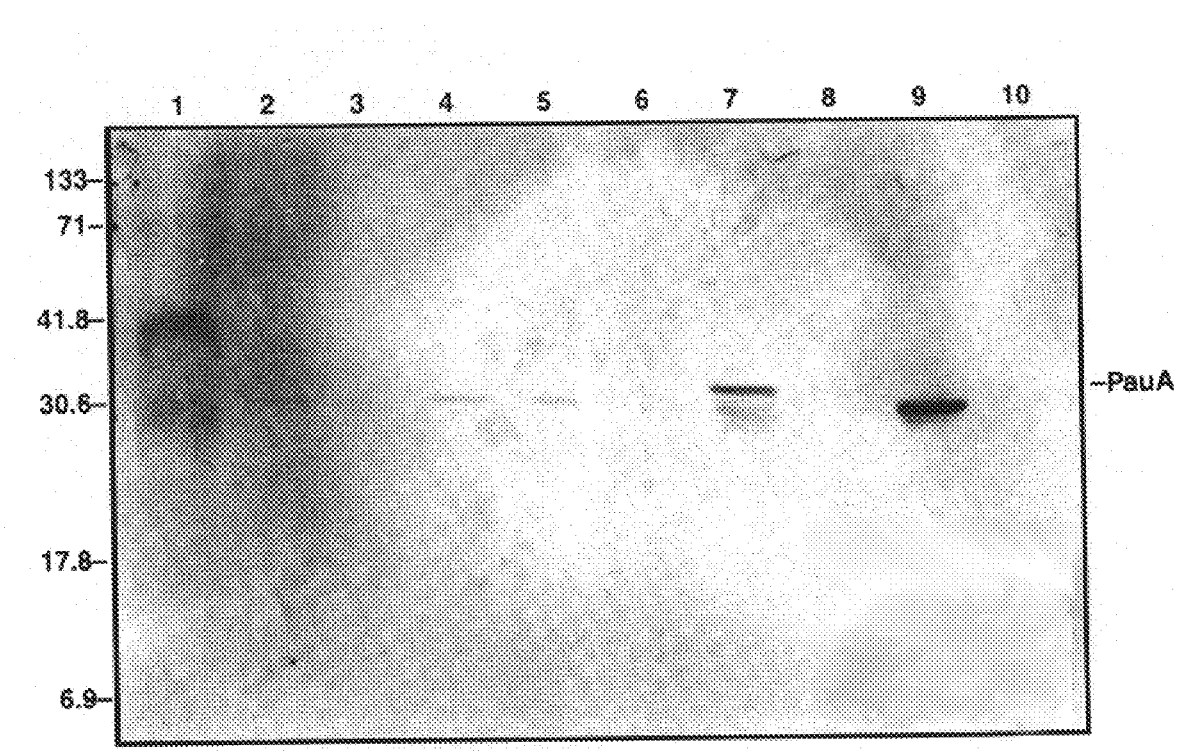

FIG. 6 Pre-induced and induced whole cell lysate pellet samples separated on SDS-PAGE and analyzed by Western blot. Lanes are the same as those in FIG. 5, except that lane 10=S. uberis strain 95–140 whole cell lysate pellet. The primary antibody was murine monoclonal antibody EC-3, and the secondary antibody was goat anti-mouse conjugated to BCIP.

5. DETAILED DESCRIPTION OF THE INVENTION

5.1. Polynucleotide Molecules Encoding A Plasminogen Activating Protein

The present invention provides an isolated polynucleotide molecule comprising a nucleotide sequence encoding a biologically active plasminogen-activating protein (designated herein as a "PauA protein," previously designated as "PA" or "streptokinase"). As used herein, the term "biologically active" refers to the ability to convert a mammalian plasminogen to plasmin. The PauA protein encoded by a polynucleotide molecule of the present invention may be the same as the PauA protein derived from any organism that produces a PauA protein, but is preferably derived from a bacterium that causes or contributes to mastitis in a member of a mammalian species. In a preferred embodiment, the genus of bacterium is Streptococcus, more preferably S. uberis or S. dysgalactiae, and the PauA protein is capable of converting bovine plasminogen to plasmin.

As used herein, the terms "polynucleotide molecule," "coding sequence," "polynucleotide sequence," "open-reading frame (ORF)," and the like, are intended to refer to both DNA and RNA molecules, which may either be single-stranded or double-stranded, and which can be transcribed and translated (DNA), or translated (RNA), into a corresponding PauA protein, or a polypeptide which is substantially homologous to a PauA protein, or a peptide fragment of either the aforementioned PauA protein or substantially homologous polypeptide, or a fusion protein or analog, in an appropriate host cell expression system when placed under the control of appropriate regulatory elements. The boundaries of the coding sequence are generally determined by the presence of a start codon at the 5' (amino) terminus and a translation stop codon at the 3' (carboxy) terminus. A coding sequence can include but is not limited to prokaryotic sequences, cDNA sequences, genomic DNA sequences, and chemically synthesized DNA and RNA sequences. As used herein, the term "ORF" refers to the minimal nucleotide sequence required to encode a PauA protein, substantially homologous polypeptide, peptide fragment, fusion protein or analog of the present invention, without any intervening termination codons.

The deduced amino acid sequences of native PauA proteins from S. uberis strains c216 and 95–140 are presented as SEQ ID NO:2 and SEQ ID NO:4, respectively. The first twenty-five amino acids of each deduced amino acid sequence presented in SEQ ID NO:2 and SEQ ID NO:4 appear to represent a signal sequence encoded by the respective pauA genes, which signal sequence is removed during cellular processing to produce the secreted (mature) PauA protein. Thus, in a preferred embodiment, the isolated polynucleotide molecule of the present invention comprises a nucleotide sequence encoding a PauA protein comprising the amino acid sequence from about amino acid position 26 (Ile) to about amino acid position 286 (Pro) of SEQ ID NO:2 or SEQ ID NO:4.

The nucleotide coding sequences of two different polynucleotide (DNA) molecules, the first encoding a PauA protein from S. uberis strain c216, and the second encoding a PauA protein from S. uberis strain 95–140, are presented as SEQ ID NO.1 and SEQ ID NO:3, respectively. The nucleotide sequence of SEQ ID NO:1 has an ORF from nt 120 to 980. The nucleotide sequence of SEQ ID NO:3 has an ORF from nt 121 to 981. Taking the removal of the peptide signal sequence into account, in a non-limiting embodiment the polynucleotide molecule of the present invention comprises a nucleotide sequence from about nucleotide position 195 to about nucleotide position 977 of SEQ ID NO:1, or from about nucleotide position 196 to about nucleotide position 978 of SEQ ID NO:3, respectively.

In a further preferred embodiment, the polynucleotide molecule of the present invention comprises a nucleotide sequence encoding an amino acid sequence comprising the amino acid sequence from about amino acid position 1 (Met) to about amino acid position 286 (Pro) of SEQ ID NO:2 or SEQ ID NO:4. In a further non-limiting embodiment, the polynucleotide molecule of the present invention comprises the nucleotide sequence from about nucleotide position 120 to about nucleotide position 980 of SEQ ID NO:1, or from about nucleotide position 121 to about nucleotide position 981 of SEQ ID NO:3, respectively. In a further non-limiting embodiment, the polynucleotide molecule of the present invention comprises the nucleotide sequence of SEQ ID NO:1, or the nucleotide sequence of SEQ ID NO:3, respectively.

Polynucleotide molecules of the present invention can further comprise nucleotide sequences that flank the ORF of SEQ ID NO:1 or SEQ ID NO:3, as presented therein.

The present invention further provides an isolated polynucleotide molecule that is substantially homologous to the polynucleotide molecule of the present invention encoding a PauA protein. As used herein to refer to a polynucleotide molecule, the term "substantially homologous" refers to a polynucleotide molecule comprising a nucleotide sequence: (a) that encodes the same PauA protein as a polynucleotide molecule comprising the nucleotide sequence from nucleotide position 195 to nucleotide position 977 of SEQ ID NO:1, or from nucleotide position 196 to nucleotide position 978 of SEQ ID NO:3, but which substantially homologous polynucleotide molecule includes one or more silent changes to the nucleotide sequence due to the degeneracy of the genetic code; and/or (b) that is at least about 70%, more preferably at least about 80%, and most preferably at least about 90% the same as that of the nucleotide sequence from nucleotide position 195 to nucleotide position 977 of SEQ ID NO:1, or from nucleotide position 196 to nucleotide position 978 of SEQ ID NO:3, and that is useful in practicing the present invention; and/or (c) that hybridizes to a DNA molecule comprising a nucleotide sequence complementary to the nucleotide sequence from nucleotide position 195 to nucleotide position 977 of SEQ ID NO:1, or from nucleotide position 196 to nucleotide position 978 of SEQ ID NO:3, under moderately stringent conditions, i.e., hybridization to filter-bound DNA in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds.), 1989, Current Protocols in Molecular Biology, Vol. I, Green Publishing Associates, Inc., and John Wiley & Sons, Inc., New York, at p. 2.10.3), and that is useful in practicing the present invention. In a preferred embodiment, the substantially homologous polynucleotide molecule hybridizes to a DNA molecule comprising a nucleotide sequence complementary to the nucleotide sequence from nucleotide position 195 to nucleotide position 977 of SEQ ID NO:1, or from nucleotide position 196 to nucleotide position 978 of SEQ ID NO:3, under highly stringent conditions, i.e., hybridization to filter-bound DNA in 0.5 M $NaHPO_4$, 7% SDS, 1 mM EDTA at 65° C., and washing in 0.1×SSC/0.1% SDS at 68° C. (Ausubel, et al., 1989, above), and is useful in practicing the present invention.

As used herein, a polynucleotide molecule is "useful in practicing the present invention" where the polynucleotide molecule either: (a) encodes a polypeptide that is biologically active, i.e., can convert a mammalian plasminogen to plasmin; or (b) encodes a polypeptide that is immunogenic, i.e., is capable of inducing a protective response against mastitis when administered to a member of a mammalian species; or (c) encodes a polypeptide that is capable of inducing the production of PauA protein-specific antibodies when administered to a member of a mammalian species; or (d) can be used as a diagnostic reagent to detect infection of a mammal with a mastitis-causing pathogen such as S. uberis by detecting the presence of a pathogen-specific polynucleotide molecule in a tissue or fluid sample from the infected mammal.

The present invention further provides a polynucleotide molecule comprising a nucleotide sequence that encodes a polypeptide that is substantially homologous to a PauA protein encoded by a polynucleotide molecule of the present invention.

As used herein to refer to polypeptides, the term "substantially homologous" refers to a polypeptide comprising an amino acid sequence: (a) that is at least about 50%, preferably at least about 70%, and most preferably at least about 80% the same as that of a PauA protein comprising the amino acid sequence from about amino acid position 26 to about amino acid position 286 of SEQ ID NO:2 or SEQ ID NO:4, and that is useful in practicing the present invention; and/or (b) that is otherwise the same as that of a PauA protein comprising the amino acid sequence from about amino acid position 26 to about amino acid position 286 of SEQ ID NO:2 or SEQ ID NO:4, but in which one or more amino acid residues have been conservatively substituted with a different amino acid residue, where such conservative substitution results in a polypeptide that is useful in practicing the present invention; and/or (c) that is otherwise the same as that of a PauA protein comprising the amino acid sequence from about amino acid position 26 to about amino acid position 286 of SEQ ID NO:2 or SEQ ID NO:4, but in which one or more amino acid residues have been non-conservatively substituted with a different amino acid residue, where such non-conservative substitution results in a polypeptide that is useful in practicing the present invention.

Conservative amino acid substitutions are well-known in the art. For example, one or more amino acid residues of a native PauA protein of the present invention can be conservatively substituted with an amino acid residue of similar charge, size or polarity, with the resulting polypeptide remaining useful in practicing the present invention. Rules for making such substitutions include those described by Dayhof, M.D., 1978, Nat. Biomed. Res. Found., Washington, D.C., Vol. 5, Sup. 3, among others. More specifically, conservative amino acid substitutions are those that generally take place within a family of amino acids that are related in their side chains. Genetically encoded amino acids are generally divided into four groups: (1) acidic= aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan and tyrosine are also jointly classified as aromatic amino acids. One or more replacements within any particular group, e.g., of a leucine with an isoleucine or valine, or of an aspartate with aglutamate, or of a threonine with a serine, or of any other amino acid residue with a structurally related amino acid residue, will generally have an insignificant effect on the function of the resulting polypeptide.

Examples of several specific, non-conservative amino acid substitutions are observed when comparing the deduced amino acid sequences of the PauA proteins from *S. uberis* strains c216 (SEQ ID NO:2) and 95–140 (SEQ ID NO:4), as summarized in TABLE 1 in Section 6.7 below. For example, the amino acid at position 73 of PauA from *S. uberis* strain c216 is aspartic acid (acidic), and from *S. uberis* strain 95–140 is asparagine (neutral, polar). In addition, the amino acid at positions 115 and 124 of PauA from *S. uberis* strain c216 is glutamine (neutral, polar), and from *S. uberis* strain 95–140 is arginine (basic). In addition, the amino acid at position 211 of PauA from *S. uberis* strain c216 is leucine (non-polar), and from *S. uberis* strain 95–140 is arginine (basic). In addition, the amino acid at position 240 of PauA from *S. uberis* strain c216 is glutamine (neutral, polar), and from *S. uberis* strain 95–140 is proline (non-polar). In addition, the amino acid at position 242 of PauA from *S. uberis* strain c216 is histidine (basic), and from *S. uberis* strain 95–140 is aspartic acid (acidic).

As used herein, a polypeptide is "useful in practicing the present invention" where the polypeptide either: (a) is biologically active, i.e., can convert a mammalian plasminogen to plasmin; or (b) is immunogenic, i.e., is capable of inducing a protective response against mastitis when administered to a member of a mammalian species; or (c) is capable of inducing the production of anti-PauA protein-specific antibodies when administered to a member of a mammalian species, which antibodies are useful as diagnostic reagents; or (d) can be used as a diagnostic reagent to detect the presence of anti-PauA protein-specific antibodies in a blood or serum sample from a mammal as the result of infection with a mastitis-causing pathogen such as *S. uberis*, or as the result of vaccination by a vaccine of the present invention.

The present invention further provides a polynucleotide molecule consisting of a nucleotide sequence encoding a peptide fragment of a PauA protein or substantially homologous polypeptide of the present invention. As used herein, the term "peptide fragment" refers to a polypeptide consisting of a sub-sequence of the amino acid sequence of a PauA protein or substantially homologous polypeptide of the present invention, which sub-sequence is shorter in length than the full-length PauA protein or substantially homologous polypeptide, and that is useful in practicing the present invention, as usefulness is defined above for polypeptides. Thus, where the full-length of the PauA protein or substantially homologous polypeptide is represented as having "n" amino acid residues, a peptide fragment thereof would be any polypeptide smaller than the full-length PauA protein or substantially homologous polypeptide, including a polypeptide having n-1 amino acid residues, where the peptide fragment is useful in practicing the present invention. Peptide fragments of the present invention are preferably at least about 7 to 10 amino acid residues in length. In a preferred embodiment, the peptide fragment comprises an amino acid sequence that represents an epitope of the PauA protein.

In a specific though non-limiting embodiment, the present invention provides a polynucleotide molecule consisting of a nucleotide sequence encoding a peptide fragment consisting of a sub-sequence of amino acids from SEQ ID NO:2 or SEQ ID NO:4 selected from the group consisting of amino acids at positions of about 28 to about 286, about 104 to about 286, about 172 to about 286, about 28 to about 170, about 104 to about 170, about 104 to about 208, about 172 to about 208, about 28 to about 103, about 28 to about 208, and about 149 to about 286.

Where the encoded peptide fragment comprises more than one sub-sequence of a PauA protein or substantially homologous polypeptide thereof, the polynucleotide molecule encoding such peptide fragment can be fashioned so that the several sub-sequences are brought together and made contiguous to each other in the peptide fragment where they were previously non-contiguous in the native PauA protein or substantially homologous polypeptide. Polypeptides having deletions of one or more internal amino acid residues as compared to a full-length PauA protein or substantially homologous polypeptide of the present invention are considered by this definition to be peptide fragments, and are included within the scope of the present invention. In addition, a polynucleotide molecule encoding a peptide fragment of the present invention may be fashioned so that different sub-sequences comprising the peptide fragment encoded thereby are arranged to have a different relative order to each other compared to that found in the native protein or substantially homologous polypeptide. In a preferred embodiment, the polynucleotide molecule encodes one or more sub-sequences of a PauA protein or substantially homologous polypeptide of the present invention, which sub-sequences represent one or more epitopic regions of the PauA protein or substantially homologous polypeptide against which neutralizing antibodies can be raised in a member of a mammalian species. The present invention is also intended to include polynucleotide molecules encoding full-length (n) PauA proteins or substantially homologous polypeptides thereof, in which sub-sequences of the amino acid sequence have been rearranged relative to one another.

The present invention further provides a polynucleotide molecule comprising a nucleotide sequence encoding a PauA protein, substantially homologous polypeptide, or peptide fragment of the present invention fused to a polypeptide carrier or fusion partner to form a fusion protein. Non-limiting examples of fusion proteins encoded by a polynucleotide molecule of the present invention include β-galactosidase fusions, trpE fusions, maltose-binding protein fusions, glutathione-S-transferase (GST) fusions, and polyhistidine fusions (carrier regions). In a specific though non-limiting embodiment, the present invention provides a polynucleotide molecule encoding a GST fusion to a peptide fragment of the present invention, said peptide fragment consisting of a sub-sequence of amino acids from SEQ ID NO:2 or SEQ ID NO:4 selected from the group consisting of amino acids at positions of about 28 to about 286, about 104 to about 286, about 172 to about 286, about 28 to about 170, about 104 to about 170, about 104 to about 208, about 172 to about 208, about 28 to about 103, about 28 to about 208, and about 149 to about 286. Methods known in the art can be used to construct polynucleotide molecules having nucleotide sequences that encode these and other fusion proteins.

All subsequent references to "PauA polypeptide" are intended to include the aforementioned PauA proteins, substantially homologous polypeptides, peptide fragments and fusion proteins of the present invention, unless otherwise indicated.

The present invention further provides oligonucleotide molecules that hybridize to any of the aforementioned polynucleotide molecules of the present invention, or that hybridize to a polynucleotide molecule having a nucleotide sequence that is the complement of any of the aforementioned polynucleotide molecules of the present invention. Such oligonucleotide molecules are preferably at least about 10 to 15 nucleotides in length, but can extend up to the length of any sub-sequence of SEQ ID NO:1 or SEQ ID NO:3, and can hybridize to one or more of the aforementioned polynucleotide molecules under moderately or highly stringent conditions. For shorter oligonucleotide molecules, an example of highly stringent conditions includes washing in 6×SSC/0.5% sodium pyrophosphate at about 37° C. for ~14-base oligos, at about 48° C. for ~17-base oligos, at about 55° C. for ~20-base oligos, and at about 60° C. for ~23base oligos. For longer oligonucleotide molecules (i.e., greater than about 100 nts), examples of moderately and highly stringent conditions are described above for substantially homologous polynucleotide molecules. Hybridization conditions can be appropriately adjusted as known in the art, depending upon the particular oligonucleotide molecules utilized.

In a preferred embodiment, an oligonucleotide molecule of the present invention hybridizes under highly stringent conditions to a polynucleotide molecule consisting of the nucleotide sequence of SEQ ID NO:1 or SEQ ID NO:3, or to a polynucleotide molecule consisting of a nucleotide sequence that is the complement of the nucleotide sequence of SEQ ID NO:1 or SEQ ID NO:3.

In a non-limiting embodiment, an oligonucleotide molecule of the present invention consists of a nucleotide sequence selected from the group consisting of SEQ ID NOS:13–27 and the complements of said sequences. In a further non-limiting embodiment, an oligonucleotide molecule of the present invention comprises a nucleotide sequence selected from the group consisting of SEQ ID NOS:13–27 and the complements of said sequences.

The oligonucleotide molecules of the present invention are useful for a variety of purposes, including as primers in amplification of a PauA protein-encoding polynucleotide molecule for use, e.g., in differential disease diagnosis, or to encode or act as antisense molecules useful in gene regulation. Amplification can be used to detect the presence of a polynucleotide molecule encoding a PauA protein in a tissue or fluid sample, e.g., in mammalian milk, from an infected animal. The production of a specific amplification product indicates the presence of bacterial infection, while lack of an amplified product can indicate a lack of infection.

Amplification can be carried out using suitably designed oligonucleotide molecules in conjunction with standard techniques, such as the polymerase chain reaction (PCR), although other amplification techniques known in the art, e.g., the ligase chain reaction, can also be used. For example, for PCR, a mixture comprising suitably designed primers, a template comprising the nucleotide sequence to be amplified, and appropriate PCR enzymes and buffers, is prepared and processed according to standard protocols to amplify a specific pauA-related polynucleotide sequence of the template.

Production and manipulation of the polynucleotide molecules and oligonucleotide molecules of the present invention are within the skill in the art and may be carried out according to recombinant techniques described, among other places, in Maniatis, et aL, 1989, *Molecular Cloning, A Laboratory Manual*, Cold Spring Harbor Laboratory Press, Cold Spring Harbor, N.Y.; Ausubel, et al., 1989, *Current Protocols In Molecular Biology*, Greene Publishing Associates & Wiley Interscience, N.Y.; and Sambrook, et al., 1989, *Molecular Cloning: A Laboratory Manual*, 2d ed., Cold Spring Harbor Laboratory Press, Cold Spring Harbor, N.Y., all of which are incorporated herein by reference. Methods for conducting PCR are described, among other places, in Innis, et al. (eds), 1995, *PCR Strategies*, Academic Press, Inc., San Diego; and Erlich (ed), 1992, *PCR Technology*, Oxford University Press, New York, which are incorporated herein by reference.

5.2. Recombinant Expression Systems 5.2.1. Expression Vectors

The present invention further provides recombinant cloning vectors and recombinant expression vectors comprising a polynucleotide molecule of the present invention. Expression vectors are preferably constructed so that the coding sequence of the polynucleotide molecule (referred to hereinafter as the "PauA coding sequence") is in operative association with one or more regulatory elements necessary for transcription and translation of the PauA coding sequence to produce a polypeptide.

As used herein, the term "regulatory element" includes but is not limited to nucleotide sequences that encode inducible and non-inducible promoters, enhancers, operators and other elements known in the art that serve to drive and/or regulate expression of polynucleotide coding sequences. Also, as used herein, the PauA coding sequence is in "operative association" with one or more regulatory elements where the regulatory elements effectively regulate and allow for the transcription of the PauA coding sequence or the translation of its mRNA, or both.

A variety of expression vectors, preferably those which contain the necessary regulatory elements for directing the replication, transcription, and translation of the PauA coding sequence, are known and can be utilized to express the PauA coding sequence. Expression vectors include recombinant bacteriophage DNA, plasmid DNA and cosmid DNA expression vectors containing the PauA coding sequence for transformation of bacteria or yeast; recombinant virus expression vectors, e.g., baculovirus, containing the PauA coding sequence for transfection of insect cells; and recombinant virus expression vectors, e.g., adenovirus or vaccinia virus, containing the PauA coding sequence for transfection of animal cells, among others.

Typical prokaryotic expression vector plasmids which can be engineered to contain the PauA coding sequence of the present invention include pUC8, pUC9, pBR322 and pBR329 (Biorad Laboratories, Richmond, Calif.), and pPL and pKK223 (Pharmacia, Piscataway, N.J.), among many others.

Methods are well-known in the art for constructing expression vectors containing particular coding sequences in operative association with appropriate regulatory elements, and these can be used to practice the present invention. These methods include in vitro recombinant techniques, synthetic techniques, and in vivo genetic recombination. See, e.g., the techniques described in Maniatis, et al., 1989, above; Ausubel, et al., 1989, above; and Sambrook, et al., 1989, above.

The regulatory elements of these vectors can vary in their strength and specificities. Depending on the host/vector system utilized, any of a number of suitable transcription and translation elements can be used. For instance, when cloning in mammalian cell systems, promoters isolated from the genome of mammalian cells, e.g., mouse metallothionein promoter, or from viruses that grow in these cells, e.g., vaccinia virus 7.5K promoter or Moloney murine sarcoma virus long terminal repeat, can be used. Promoters obtained by recombinant DNA or synthetic techniques can also be used to provide for transcription of the inserted sequence. In addition, expression from certain promoters can be elevated in the presence of particular inducers, e.g., zinc and cadmium ions for metallothionein promoters.

Non-limiting examples of transcriptional regulatory regions or promoters include for bacteria, the β-gal promoter, the T7 promoter, the TAC promoter, λ left and right promoters, trp and lac promoters, trp-lac fusion promoters, etc.; for yeast, glycolytic enzyme promoters, such as ADH-I and -II promoters, GPK promoter, PGI promoter, TRP promoter, etc.; for mammalian cells, SV40 early and late promoters, adenovirus major late promoters, etc.

Specific initiation signals are also required for sufficient translation of the inserted PauA coding sequence. These signals typically include an ATG initiation codon and adjacent sequences. In cases where the entire PauA gene, including its own initiation codon and adjacent sequences, are inserted into the appropriate expression vector, no additional translation control signals may be needed. However, in cases where only a portion of the coding sequence is inserted, exogenous translational control signals, including the ATG initiation codon, may be required. These exogenous translational control signals and initiation codons can be obtained from a variety of sources, both natural and synthetic. Furthermore, the initiation codon must be in phase with the reading frame of the PauA coding sequence to ensure in-frame translation of the entire insert.

Fusion protein expression vectors can be used to express a fusion protein comprising a PauA protein, substantially homologous polypeptide, or peptide fragment fused to a carrier or fusion partner. The purified fusion protein can be used, e.g., to raise antisera against a PauA protein for use as a diagnostic reagent, to study the biochemical properties of a PauA protein, to engineer a PauA fusion protein with altered biological activity, or to aid in the identification or purification of an expressed PauA protein. Possible fusion protein expression vectors include but are not limited to vectors incorporating sequences that encode β-galactosidase and trpE fusions, maltose-binding protein fusions, glutathione-S-transferase (GST) fusions and polyhistidine fusions (carrier regions). Specific examples of GST-peptide fragment fusions are described in Section 5.1 above, and the present invention provides expression vectors comprising polynucleotide molecules having nucleotide sequences that encode each of them. Methods known in the art can be used to construct expression vectors encoding such PauA fusion proteins.

A PauA fusion protein can be engineered to comprise a region useful for purification. For example, PauA-maltose-binding protein fusions can be purified using amylose resin; PauA-GST fusion proteins can be purified using glutathione-agarose beads; and PauA-polyhistidine fusions can be purified using divalent nickel resin. Alternatively, antibodies against a carrier protein or peptide can be used for affinity chromatography purification of the fusion protein. For example, a nucleotide sequence coding for the target epitope of a monoclonal antibody can be engineered into the expression vector in operative association with the regulatory elements and situated so that the expressed epitope is fused to the PauA partner of the fusion protein. For example, a nucleotide sequence coding for the FLAG™ epitope tag (International Biotechnologies Inc.), which is a hydrophilic marker peptide, can be inserted by standard techniques into the expression vector at a point corresponding to the amino or carboxyl terminus of the PauA partner. The expressed PauA-FLAG™ epitope fusion product can then be detected and affinity-purified using commercially available anti-FLAG™ antibodies.

The expression vector can also be engineered to contain polylinker sequences that encode specific protease cleavage sites so that the expressed PauA partner can be released from the carrier region or fusion partner by treatment with a specific protease. For example, the fusion protein vector can include DNA sequences encoding thrombin or factor Xa cleavage sites, among others.

A signal sequence upstream from, and in reading frame with, the PauA coding sequence can be engineered into the expression vector by known methods to direct the trafficking and secretion of the expressed protein. Non-limiting examples of signal sequences include those from α-factor, immunoglobulins, outer membrane proteins, penicillinase, T-cell receptors, as well as that of the native PauA protein itself, among others.

To aid in the selection of host cells transformed or transfected with the expression vector of the present invention, the expression vector can be engineered to further comprise a coding sequence for a reporter gene product or other selectable marker. Such a coding sequence is preferably in operative association with the regulatory element coding sequences, as described above. Reporter genes which can be useful in practicing the present invention are well-known in the art and include those encoding chloramphenicol acetyltransferase (CAT), green fluorescent protein, firefly luciferase, and human growth hormone, among others. Nucleotide sequences encoding selectable markers are well-known in the art, and include those that encode gene products conferring resistance to antibiotics or antimetabolites, or that supply an auxotrophic requirement. Examples of such sequences include those that encode thymidine kinase activity, or resistance to methotrexate, ampicillin, kanamycin, chloramphenicol, or zeocin, among many others.

5.2.2. Transformation of Host Cells

The present invention further provides host cells transformed with a recombinant cloning or expression vector of the present invention, and cell lines derived therefrom. Host cells useful in the practice of the present invention can be either prokaryotic or eukaryotic. Such transformed host cells include but are not limited to microorganisms, such as bacteria transformed with recombinant bacteriophage DNA, plasmid DNA or cosmid DNA expression vectors, or yeast transformed with recombinant expression vectors; or animal cells, such as insect cells transfected with recombinant virus expression vectors, e.g., baculovirus, or mammalian cells transfected with recombinant virus expression vectors, e.g., adenovirus or vaccinia virus, among others.

Bacterial. cells are generally preferred as host cells. A strain of E. coli can typically be used, such as, e.g., the DH5α strain, available from the American Type Culture Collection (ATCC), Rockville, Md., USA (Accession No. 31343) or from commercial sources (Stratagene), or the TAP56 or LW14 strains (Pfizer in-house strains of E. coli). Preferred eukaryotic host cells include yeast cells, although mammalian cells, such as from a mouse, hamster, cow, monkey, or human fibroblast cell line, can also be utilized effectively. Examples of eukaryotic host cells that can be used to express the recombinant PauA polypeptide of the present invention include Chinese hamster ovary (CHO) cells (e.g., ATCC Accession No. CCL61), and NIH Swiss mouse embryo cells NIH/3T3 (e.g., ATCC Accession No. CRL 1658).

The recombinant vector of the present invention is preferably transformed or transfected into one or more host cells of a substantially homogeneous culture of cells. The vector is generally introduced into host cells in accordance with known techniques, such as, e.g., by calcium phosphate precipitation, calcium chloride treatment, microinjection, electroporation, transfection by contact with a recombined virus, liposome-mediated transfection, DEAE-dextran transfection, transduction, conjugation, or microprojectile bombardment. Selection of transformants can be conducted by standard procedures, such as by selecting for cells expressing a selectable marker, e.g., antibiotic resistance, associated with the recombinant vector.

Once a recombinant vector of the present invention is introduced into the host cell, the integration and maintenance of the PauA coding sequence either in the host cell genome or episomally can be confirmed by standard techniques, e.g., by Southern hybridization analysis, restriction enzyme analysis, PCR analysis, including reverse transcriptase PCR (rt-PCR), or by immunological assay to detect the expected polypeptide product. Host cells containing and/or expressing the recombinant PauA coding sequence can be identified by any of at least four general approaches, which are well-known in the art, including. (i) DNA-DNA, DNA-RNA, or RNA-antisense RNA hybridization; (ii) detecting the presence of "marker" gene functions; (iii) assessing the level of transcription as measured by the expression of PauA-specific mRNA transcripts in the host cell; and (iv) detecting the presence of mature PauA polypeptide product as measured, e.g., by immunoassay or by the presence of PauA biological activity (i.e., the conversion of an appropriate mammalian plasminogen to plasmin).

In a non-limiting example, the biological activity of a recombinantly-expressed PauA polypeptide can be monitored by detecting the conversion of bovine plasminogen to plasmin using, e.g., an agarose/skim-milk overlay assay, such as that described in International Patent Publication WO 93/14209. Briefly, a preparation to be tested for PauA biological activity is diluted to an appropriate concentration, e.g., 1 μg protein/ml in phosphate buffered saline (PBS) (pH 7.4), and added to a well cut into a sheet of agarose (1% w/v in PBS), which agarose contains Oxoid™ skim-milk (1% w/v; Unipath Ltd., Hampshire, England) and bovine plasminogen ($10^{-3}$ units/ml) (Sigma). The presence of a biologically active PauA polypeptide is detected by observing the formation of a zone of clearing in the skim-milk layer, which indicates the conversion of bovine plasminogen to plasmin followed by the breakdown of milk proteins. Alternatively, a chromogenic assay, such as that described in Section 7.3 below, can be used.

5.2.3. Expression and Characterization of Recombinant Polypeptides

Once the PauA coding sequence has been stably introduced into an appropriate host cell, the transformed host cell is clonally propagated, and the resulting cells are grown under conditions conducive to the maximum production of the PauA polypeptide. Such conditions typically include growing cells to high density. Where the expression vector comprises an inducible promoter, appropriate induction conditions such as, e.g., temperature shift, exhaustion of nutrients, addition of gratuitous inducers (e.g., analogs of carbohydrates, such as isopropyl-β-D-thiogalactopyranoside (IPTG)), accumulation of excess metabolic by-products, or the like, are employed as needed to induce expression.

Where the expressed PauA polypeptide is retained inside the host cells, the cells are harvested and lysed, and the product isolated and purified from the lysate under extraction conditions known in the art to minimize protein degradation such as, e.g., at 4° C., or in the presence of protease inhibitors, or both. Where the expressed PauA polypeptide is secreted from the host cells, the exhausted nutrient medium can simply be collected and the product isolated therefrom.

The expressed PauA polypeptide can be substantially purified or isolated from cell lysates or culture medium, as appropriate, using standard methods, including but not limited to any combination of the following methods: ammonium sulfate precipitation, size fractionation, ion exchange chromatography, HPLC, density centrifugation, and affinity chromatography. Where the expressed PauA polypeptide exhibits biological activity, i.e., the ability to activated plasminogen, increasing purity of the preparation can be monitored at each step of the purification procedure by use of an assay, such as, e.g., the agarose/skim-milk overlay assay described above, or the chromogenic assay described in Section 7.3 below, or by any other relevant assay that detects plasminogen activation. If the expressed polypeptide lacks biological activity, it can be detected as based, e.g., on size, or reactivity with an antibody otherwise specific for the PauA polypeptide, or by the presence of a fusion tag.

Thus, the present invention further provides a method for preparing a PauA polypeptide, comprising culturing a host cell transformed with a recombinant expression vector, said recombinant expression vector comprising a polynucleotide molecule comprising a nucleotide sequence encoding: (a) a PauA protein comprising the amino acid sequence from about amino acid position 26 to about amino acid position 286 of SEQ ID NO:2 or SEQ ID NO:4; or (b) a polypeptide that is substantially homologous to the PauA protein; or (c) a peptide fragment of the PauA protein or substantially homologous polypeptide; or (d) a fusion protein comprising the PauA protein, substantially homologous polypeptide, or peptide fragment fused to a fusion partner, which polynucleotide molecule is in operative association with one or more regulatory elements that control expression of the polynucleotide molecule in the host cell, under conditions conducive to the production of the PauA polypeptide, and recovering the PauA polypeptide from the cell culture.

Once a PauA polypeptide of sufficient purity has been obtained, it can be characterized by standard methods, including by SDS-PAGE, size exclusion chromatography, amino acid sequence analysis, biological activity in converting plasminogen to plasmin, etc. The amino acid sequence of the PauA polypeptide can be determined using standard peptide sequencing techniques. The PauA polypeptide can be further characterized using hydrophilicity analysis (see, e.g., Hopp and Woods, 1981, Proc. Natl. Acad. Sci. USA 78:3824), or analogous software algorithms, to identify hydrophobic and hydrophilic regions of the PauA polypeptide. Structural analysis can be carried out to identify regions of the PauA polypeptide that assume specific secondary structures. Biophysical methods such as X-ray crystallography (Engstrom, 1974, Biochem. Exp. Biol. 11: 7–13), computer modelling (Fletterick and Zoller (eds), 1986, in: *Current Communications in Molecular Biology*, Cold Spring Harbor Laboratory, Cold Spring Harbor, N.Y.), and nuclear magnetic resonance (NMR) can be used to map and study sites of interaction between the PauA polypeptide and its substrate. Information obtained from these studies can be used to design more effective vaccine compositions, to select vaccines comprising only specific portions of the PauA polypeptide, or to design or select therapeutic or pharmacologic compounds that can block the activation of plasminogen by a native PauA protein.

PauA polypeptides that are useful in practicing the present invention are those that: (a) are biologically active, i.e., can convert a mammalian plasminogen to plasmin; or (b) are immunogenic, i.e., capable of inducing a protective response against mastitis when administered to a member of a mammalian species; or (c) are capable of inducing the production of anti-PauA protein-specific antibodies when administered to a member of a mammalian species, which antibodies are useful as diagnostic reagents; or (d) can be used as diagnostic reagents to detect the presence of anti-PauA protein-specific antibodies in a blood or serum sample from a mammal resulting from infection with a mastitis-causing pathogen such as *S. uberis*, or resulting from vaccination with a vaccine of the present invention. Such polypeptides, once prepared, can be identified using nothing more than routine screening procedures known in the art. For example, the ability to convert a mammalian plasminogen to plasmin can be determined using one of the bioassays described herein. The ability to induce a protective immune response against mastitis can be identified by administering the PauA polypeptide to a member of a mammalian species susceptible to mastitis caused by a species of Streptococcus such as *S. uberis*, and testing for the presence of PauA neutralizing antibodies, or for the ability of the vaccinated animal to resist subsequent challenge with the mastitis-causing pathogen. The ability to induce the production of PauA protein-specific antibodies can be identified by administering the PauA polypeptide to a model animal, such as a mouse, pig, sheep, goat, horse, cow, etc., and testing the animal for seroconversion using standard techniques. The ability to use the PauA polypeptide as a diagnostic reagent can be determined by exposing the PauA polypeptide to a blood or serum sample of an animal previously infected with a mastitis-causing pathogen such as *S. uberis*, or previously vaccinated with a vaccine of the present invention, and detecting binding to the PauA polypeptide of PauA protein-specific antibodies from the sample using standard techniques, such as with an ELISA assay.

Specific though non-limiting examples of PauA polypeptides useful in practicing the present invention include proteins comprising the amino acid sequence from about amino acid position 26 to about amino acid position 286 of SEQ ID NO:2 or SEQ ID NO:4, or from about amino acid position 1 to about amino acid position 286 of SEQ ID NO:2 or SEQ ID NO:4.

Specific though non-limiting examples of PauA peptide fragments useful in practicing the present invention include a peptide fragment consisting of a sub-sequence of amino acids from SEQ ID NO:2 or SEQ ID NO:4 selected from the group consisting of amino acids at positions of about 28 to about 286, about 104 to about 286, about 172 to about 286, about 28 to about 170, about 104 to about 170, about 104 to about 208, about 172 to about 208, about 28 to about 103, about 28 to about 208, and about 149 to about 286.

Specific though non-limiting examples of fusion proteins useful in practicing the present invention include GST fusion proteins comprising GST fused to a peptide fragment consisting of a sub-sequence of amino acids from SEQ ID NO:2 or SEQ ID NO:4 selected from the group consisting of amino acids at positions of about 28 to about 286, about 104 to about 286, about 172 to about 286, about 28 to about 170, about 104 to about 170, about 104 to about 208, about 172 to about 208, about 28 to about 103, about 28 to about 208, and about 149 to about 286.

The present invention thus provides substantially purified or isolated PauA proteins, substantially homologous polypeptides thereof, peptide fragments of such PauA proteins and substantially homologous polypeptides, and fusion proteins comprising said PauA proteins, substantially homologous polypeptides or peptide fragments (collectively referred to herein as "PauA polypeptides").

5.3. Analogs and Derivatives of PauA

The present invention further provides analogs and derivatives of the aforementioned PauA polypeptides, where such analogs and derivatives are useful in practicing the present invention, as usefulness is defined above for polypeptides.

The manipulations that result in the production of analogs can occur either at the gene level or at the protein level, or both. At the gene level, e.g., a cloned DNA molecule encoding a PauA polypeptide can be modified in vitro by one or more known strategies to encode a PauA protein analog.

Such modifications include but are not limited to endonuclease digestion, mutations that create or destroy translation, initiation, and/or termination sequences, or that create variations in the coding region, or any combination thereof. See, e.g., Maniatis, et al., 1989, above; Ausubel, et al., 1989, above; and Sambrook, et al., 1989, above. Any technique for mutagenesis known in the art can be used, including but not limited to exposure to a mutagenic agent such as radiation or a chemical mutagen, or in vitro site-directed mutagenesis (see, e.g., Hutchinson, et al., 1978, J. Biol. Chem. 253:6551).

Manipulation of the PauA polypeptide can also be made at the protein level. One or more chemical modifications of the protein can be carried out using known techniques, including but not limited to any of the following: substitution of one or more L-amino acids of the native protein with corresponding D-amino acids, amino acid analogs, or amino acid mimics, so as to produce, e.g., carbazates or tertiary centers; or specific chemical modification, such as, e.g., proteolytic cleavage with trypsin, chymotrypsin, papain or V8 protease, or treatment with $NaBH_4$ or cyanogen bromide, or acetylation, formylation, oxidation or reduction, etc.

A PauA polypeptide can be derivatized by conjugation thereto of one or more chemical groups, including but not limited to acetyl groups, sulfur bridging groups, glycosyl groups, lipids, and phosphates, and/or another PauA polypeptide, or other proteins, such as, e.g., serum albumins, keyhole limpet hemocyanin, or commercially activated BSA, or polyamino acids (e.g., polylysine), or polysaccharides, (e.g., sepharose, agarose, or modified or unmodified celluloses), among others. Such conjugation is preferably by covalent linkage at amino acid side chains and/or at the N-terminus or C-terminus of the polypeptide. Methods for carrying out such conjugation reactions are well-known in the field of protein chemistry.

Derivatives useful in practicing the present invention also include those in which a water-soluble polymer such as, e.g., polyethylene glycol, is conjugated to the PauA polypeptide, or to an analog or other derivative thereof, thereby providing additional desirable properties while retaining, at least in part, the immunogenicity of the polypeptide. These additional desirable properties include, e.g., increased solubility in aqueous solutions, increased stability in storage, increased resistance to proteolytic degradation, and increased in vivo half-life. Water-soluble polymers suitable for conjugation to a PauA polypeptide include but are not limited to polyethylene glycol homopolymers, polypropylene glycol homopolymers, copolymers of ethylene glycol with propylene glycol, wherein said homopolymers and copolymers are unsubstituted or substituted at one end with an alkyl group, polyoxyethylated polyols, polyvinyl alcohol, polysaccharides, polyvinyl ethyl ethers, and $\alpha,\beta$-poly[2-hydroxyethyl]-DL-aspartamide. Polyethylene glycol is particularly preferred. Methods for making water-soluble polymer conjugates of proteins are known in the art and are described, among other places, in U.S. Pat. Nos. 3,788,948; 3,960,830; 4,002,531; 4,055,635; 4,179,337; 4,261,973; 4,412,989; 4,414,147; 4,415,665; 4,609,546; 4,732,863; 4,745,180; European patent (EP) 152,847; EP 98,110; and Japanese patent (JP) 5,792,435, which patents are incorporated herein by reference.

Analogs and derivatives that are useful in practicing the present invention can be identified using the methods described above for PauA polypeptides.

5.4. Anti-Mastitis Vaccines

The present invention further provides a vaccine for protecting a member of a mammalian species against mastitis, comprising an immunologically effective amount of: (a) a PauA protein comprising the amino acid sequence from about amino acid position 26 to about amino acid position 286 of SEQ ID NO:2 or SEQ ID NO:4; or (b) a polypeptide that is substantially homologous to the PauA protein; or (c) a peptide fragment consisting of a subsequence of the PauA protein or substantially homologous polypeptide; or (d) a fusion protein comprising the PauA protein, substantially homologous polypeptide, or peptide fragment fused to a fusion partner; or (e) an analog or derivative of the PauA protein, substantially homologous polypeptide, peptide fragment, or fusion protein; or (f) a polynucleotide molecule comprising a nucleotide sequence encoding the PauA protein, substantially homologous polypeptide, peptide fragment, fusion protein, or analog, which protein, substantially homologous polypeptide, peptide fragment, fusion protein, analog, derivative or polynucleotide molecule is capable of inducing a protective response against mastitis in the mammal; and a veterinarily acceptable carrier.

In a non-limiting embodiment, the vaccine of the present invention comprises transformed host cells, comprising an expression vector or polynucleotide molecule of the present invention, where the expression vector or polynucleotide molecule is expressed in the host cells to produce a PauA protein, substantially homologous polypeptide, peptide fragment, fusion protein or analog of the present invention capable of inducing a protective response against mastitis in a mammal. The host cell can be any cell in which the expression vector or polynucleotide molecule of the present invention can be expressed and which cell can be administered in a vaccine to a member of a mammalian species. In a non-limiting embodiment, such host cell is an *E. coli* host cell.

As used herein, the term "immunologically effective amount" refers to an amount of immunogen, i.e., PauA protein, substantially homologous polypeptide, peptide fragment, fusion protein, analog, derivative, or polynucleotide molecule of the present invention which is capable of inducing a protective response against mastitis when administered to the mammal.

The phrase "capable of inducing a protective response" is used broadly herein to include the induction of, or increase in, any immune-based response in the mammal in response to vaccination, including either an antibody or cell-mediated immune response, or both, that serves to protect the vaccinated mammal against mastitis. The terms "protective response" and "protect" as used herein are not limited to absolute prevention of mastitis or absolute prevention of infection by a mastitis-causing pathogen, but are intended to include any reduction in the degree or rate of infection by the pathogen, or any reduction in the severity of the disease or in any symptom or condition resulting from infection with the pathogen, including any detectable increase in milk production, or any detectable prevention or slowing of decrease in milk production, as compared to an unvaccinated, infected mammal.

As used herein, the terms "member of a mammalian species" and "mammal" refer to any mammalian species or mammal that can be protected against mastitis using the vaccine of the present invention, including members of a bovine species (cows and oxen), as well as sheep, pigs, goats, horses, dogs, and cats.

Vaccine compositions of the present invention can be formulated following accepted convention using standard buffers, carriers, stabilizers, diluents, preservatives, and/or solubilizers, and can also be formulated to facilitate sustained release. Diluents can include water, saline, dextrose, ethanol, glycerol, and the like. Additives for isotonicity can include sodium chloride, dextrose, mannitol, sorbitol, and lactose, among others. Stabilizers include albumin, among others.

Adjuvants can optionally be employed in the vaccine, non-limiting examples of which include the RIBI adjuvant system (Ribi Inc.), alum, aluminum hydroxide gel, oil-in-water emulsions such as, e.g., squalene-in-water, water-in-oil emulsions such as, e.g., Freund's complete and incomplete adjuvants, Block co polymer (CytRx, Atlanta GA), SAF-M (Chiron, Emeryville Calif.), AMPHIGEN® adjuvant, saponin, other purified or semi-purified saponin fractions such as Quil A (Superfos) or QS-21 (Cambridge Biotech Inc., Cambridge Mass.), monophosphoryl lipid A, and Avridine lipid-amine adjuvant. The vaccine can further comprise one or more other immunomodulatory agents such as, e.g., interleukins, interferons, or other known cytokines.

Suitable veterinarily acceptable vaccine vehicles, carriers, and additives are known, or will be apparent to those skilled in the art; see, e.g., Remington's *Pharmaceutical Science*, 18th Ed., 1990, Mack Publishing, which is incorporated herein by reference. The vaccine may be stored in solution or, alternatively, in lyophilized form to be reconstituted with a sterile diluent solution prior to administration.

The present invention further provides vaccine formulations for the sustained release of the immunogen. Examples of such sustained release formulations include immunogen in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including A. Domb, et al., 1992, Polymers for Advanced Technologies 3: 279–292, which is incorporated herein by reference. Additional guidance in selecting and using polymers in pharmaceutical formulations can be found in the text by M. Chasin and R. Langer (eds), 1990, "Biodegradable Polymers as Drug Delivery Systems" in: *Drugs and the Pharmaceutical Sciences*, Vol. 45, M. Dekker, N.Y., which is also incorporated herein by reference. Alternatively, or additionally, the PauA polypeptides, analogs, derivatives, or polynucleotides of the vaccine of the present invention can be microencapsulated to improve administration and efficacy. Methods for microencapsulating antigens are well-known in the art, and include techniques described, e.g., in U.S. Pat. Nos. 3,137,631; 3,959,457; 4,205,060; 4,606,940; 4,744,933; 5,132,117; and International Pub. WO 95/28227, all of which are incorporated herein by reference.

Liposomes can also be used to provide for the sustained release of any of the PauA polypeptides, analogs, derivatives or polynucleotide molecules of the present invention. Details concerning how to make and use liposomal formulations can be found in, among other places, U.S. Pat. Nos. 4,016,100; 4,452,747; 4,921,706; 4,927,637; 4,944,948; 5,008,050; and 5,009,956, all of which are incorporated herein by reference.

In a non-limiting embodiment, the vaccine of the present invention can be a combination vaccine for protecting a member of a mammalian species against mastitis and, optionally, one or more other diseases or pathological conditions that can afflict the mammal, which combination vaccine comprises an immunologically effective amount of a first component comprising: a) a PauA protein comprising the amino acid sequence from about amino acid position 26 to about amino acid position 286 of SEQ ID NO:2 or SEQ ID NO:4; or (b) a polypeptide that is substantially homologous to the PauA protein; or (c) a peptide fragment consisting of a sub-sequence of the PauA protein or substantially homologous polypeptide; or (d) a fusion protein comprising the PauA protein, substantially homologous polypeptide or peptide fragment fused to a fusion partner; or (e) an analog or derivative of the PauA protein, substantially homologous polypeptide, peptide fragment, or fusion protein; or (f) a polynucleotide molecule comprising a nucleotide sequence encoding the PauA protein, substantially homologous polypeptide, peptide fragment, fusion protein, or analog, which protein, substantially homologous polypeptide, peptide fragment, fusion protein, analog, derivative or polynucleotide molecule is capable of inducing a protective response against mastitis in the mammal; an immunologically effective amount of a second component comprising an antigen capable of inducing a protective response against a disease or pathological condition that can afflict the mammal; and a veterinarily acceptable carrier.

The antigen of the second component of the combination vaccine is selected based on its ability to induce a protective response against either mastitis or another disease or pathological condition which can afflict the mammal, or against a pathogen which can infect the mammal, as known in the art. Any immunogenic composition known to be useful in a vaccine composition in the particular mammalian species can be used in the second component of the combination vaccine. Such immunogenic compositions include but are not limited to those that provide protection against bovine herpes virus (syn., infectious bovine rhinotracheitis), bovine respiratory syncitial virus, bovine viral diarrhea virus, parainfluenza virus types I, II, or III, Leptospira spp., Campylobacter spp., Staphylococcus spp., such as, e.g., *S. aureus*, Streptococcus spp., such as, e.g., *S. agalactiae* or *S. dysgalactiae*, Mycoplasma spp., Klebsiella spp., Salmonella spp., rotavirus, coronavirus, rabies, Pasteurella spp., such as, e.g., *P. haemolytica* or *P. multocida*, Clostridium spp., *Tetanus toxoid, E. coli*, Neospora spp., other eukaryotic parasites, among others.

The antigen comprising the second component can optionally be covalently linked to the PauA polypeptide, analog or derivative of the first component to produce a chimeric molecule or fusion protein. In a non-limiting embodiment, the antigen of the second component comprises a hapten, the immunogenicity of which is detectably increased by conjugation to the PauA polypeptide, analog or derivative of the first component.

Chimeric molecules comprising covalently-linked antigens of the first and second components of the combination vaccine can be synthesized using one or more techniques known in the art. For example, a chimeric molecule can be produced synthetically using a commercially available peptide synthesizer utilizing standard chemical synthetic processes (see, e.g., Merrifield, 1985, Science 232:341–347). Alternatively, the separate components can be separately synthesized and then linked together by the use of chemical linking groups, as known in the art. Alternatively, a chimeric molecule can be produced using recombinant DNA technology whereby, e.g., separate polynucleotide molecules comprising nucleotide sequences encoding the different antigens of the chimeric molecule are spliced together in-frame and expressed in a suitable transformed host cell for subsequent isolation of the chimeric molecule. Where the vaccine of the present invention comprises a polynucleotide molecule rather than a polypeptide, the spliced polynucleotide molecule can be used in the vaccine composition. Ample guidance for carrying out such recombinant techniques is provided in Maniatis, et al., 1989, above; Ausubel, et al., 1989, above; Sambrook, et al., 1989, above; Innis, et al. (eds) 1995, above; and Erlich, 1992, above.

As described above, the vaccine of the present invention can comprise transformed host cells comprising an expression vector or polynucleotide molecule of the present invention, where the expression vector or polynucleotide molecule is expressed in the host cells to produce a PauA protein, substantially homologous polypeptide, peptide fragment, fusion protein or analog of the present invention capable of inducing a protective response against mastitis in a mammal. In a further non-limiting embodiment, the combination vaccine of the present invention comprises a host cell associated as a pathogen with any disease or pathological condition other than mastitis caused by *S. uberis*, which disease or pathological condition can afflict the mammal, which host cell further comprises an expression vector or polynucleotide molecule of the present invention, where the expression vector or polynucleotide molecule is expressed in the host cell to produce a PauA protein, substantially homologous polypeptide, peptide fragment, fusion protein or analog of the present invention capable of inducing a protective response against mastitis in a mammal, and where such host cell serves to induce a protective immune response against the disease or pathological condition other than mastitis caused by *S. uberis*. In a non-limiting embodiment, such host cell is selected from the group consisting of Leptospira spp., Campylobacter spp., Staphylococcus spp., such as, e.g., *S aureus*, Streptococcus spp., such as, e.g., *S. agalactiae* or *S. dysgalactiae* Mycoplasma spp., Klebsiella spp., Salmonella spp., Pasteurella spp., such as, e.g., *P. haemolytica* or *P. multocida*, Clostridium spp., *E. coli*, Neospora spp., and other eukaryotic parasites.

The present invention further provides a method of preparing a vaccine for protecting a member of a mammalian species against mastitis, comprising combining an immunologically effective amount of: a) a PauA protein comprising the amino acid sequence from about amino acid position 26 to about amino acid position 286 of SEQ ID NO:2 or SEQ ID NO:4; or (b) a polypeptide that is substantially homologous to the PauA protein; or (c) a peptide fragment consisting of a sub-sequence of the PauA protein or substantially homologous polypeptide: or (d) a fusion protein comprising the PauA protein, substantially homologous polypeptide or peptide fragment fused to a fusion partner; or (e) an analog or derivative of the PauA protein, substantially homologous polypeptide, peptide fragment, or fusion protein; or (e a polynucleotide molecule comprising a nucleotide sequence encoding the PauA protein, substantially homologous polypeptide, peptide fragment, fusion protein, or analog, which protein, substantially homologous polypeptide , peptide fragment, fusion protein, analog, derivative or polynucleotide molecule is capable of inducing a protective response against mastitis in the mammal, with a veterinarily acceptable carrier.

The present invention further provides a method of vaccinating a member of a mammalian species against mastitis, comprising administering an immunologically effective amount of the vaccine of the present invention to the mammal.

The amount of immunogen administered to the mammal depends upon such factors as the species, age, weight, health and general physical characteristics of the animal being vaccinated, as well as the particular immunogenic and vaccine composition to be administered. Determination of the optimum dosage for each parameter may be made using routine methods in view, e.g., of empirical studies. Specifically regarding administration of a PauA polypeptide of the vaccine of the present invention to a member of a bovine species, the amount administered will preferably range from about 0.01 ;μg to about 100 mg of polypeptide, more preferably from about 0.1 μg to about 10 mg, and most preferably from about 1.0 μg to about 1 mg. Specifically regarding administration of a polynucleotide molecule of the vaccine of the present invention to a member of a bovine species, the amount administered will preferably range from about 0.05 μg to about 500 mg of polynucleotide, more preferably from about 0.5 μg to about 50 mg, and most preferably from about 5.0 μg to about 5 mg. In addition, the typical dose volume of the vaccine will range from about 50 μl to about 50 ml per dose per animal.

Vaccine regimens can also be selected based on the above-described factors. Animals can be vaccinated at any appropriate time, including at weaning age or younger, or just prior to or at the time of breeding, at calving, at dry-off, or at the time that mastitis infection first begins to appear in one or more members of a herd. Supplemental administrations, or boosters, may be required to achieve full protection. Methods for determining whether adequate immune protection has been achieved, such as by determining seroconversion or by the use of neutralization assays, are well-known in the art.

The vaccine of the present invention can be administered by any appropriate route such as, e.g., by oral, intranasal, intramuscular, intramammary, intra-lymph node, intraperitoneal, intravenous, intra-arterial, subcutaneous, rectal or vaginal administration, or by a combination of routes. The skilled artisan will readily be able to formulate the vaccine composition according to the route chosen.

The present invention further provides a vaccine kit for vaccinating a member of a mammalian species against mastitis, comprising a first container comprising an immunologically effective amount of: a) a PauA protein comprising the amino acid sequence from about amino acid position 26 to about amino acid position 286 of SEQ ID NO:2 or SEQ ID NO:4; or (b) a polypeptide that is substantially homologous to the PauA protein; or (c) a peptide fragment consisting of a sub-sequence of the PauA protein or substantially homologous polypeptide; or (d) a fusion protein comprising the PauA protein, substantially homologous polypeptide or peptide fragment fused to a fusion partner; or (e) an analog or derivative of the PauA protein, substantially homologous polypeptide, peptide fragment, or fusion protein; or (f) a polynucleotide molecule comprising a nucleotide sequence encoding the PauA protein, substantially homologous polypeptide, peptide fragment, fusion protein, or analog, which protein, polypeptide, peptide fragment, fusion protein, analog, derivative or polynucleotide molecule is capable of inducing a protective response against mastitis in the mammal; and a second container comprising a veterinarily acceptable carrier or diluent.

5.5. Anti-PauA Antibody Production

The present invention provides polyclonal and monoclonal antibodies that bind to a PauA polypeptide, analog, or derivative of the present invention. Such antibodies can be used as affinity reagents with which to purify a native or recombinant PauA polypeptide; or to detect the presence of a PauA protein, e.g., in histological sections, or in cell, tissue or fluid samples from an infected mammal, such as, e.g., by ELISA or Western blot assays; or therapeutically to neutralize native PauA protein activity in an infected animal.

Antibodies can be raised against any of the PauA polypeptides, analogs or derivatives of the present invention. Various host animals, including but not limited to cows, horses, rabbits, goats, sheep, and mice, can be used according to known methods to produce anti-PauA protein-specific antibodies. Various adjuvants, such as those listed in Section 5.4 above, can be used to enhance antibody production.

Polyclonal antibodies can be obtained from immunized animals and tested for anti-PauA polypeptide specificity using standard techniques. Alternatively, monoclonal antibodies to a PauA polypeptide can be prepared using any technique that provides for the production of antibody molecules by continuous cell lines in culture. These include but are not limited to the hybridoma technique originally described by Kohler and Milstein (Nature, 1975, 256: 495–97); the human B-cell hybridoma technique (Kosbor, et al., 1983, Immunology Today 4:72; Cote, et al., 1983, Proc. Natl. Acad. Sci. USA 80: 2026–2030); and the EBV-hybridoma technique (Cole, et al., 1985, *Monoclonal Antibodies and Cancer Therapy*, Alan R. Liss, Inc., pp. 77–96). Alternatively, techniques described for the production of single chain antibodies (see, e.g., U.S. Pat. No. 4,946,778) can be adapted to produce PauA polypeptide-specific single chain antibodies. These publications are incorporated herein by reference.

Antibody fragments that contain specific binding sites for a PauA polypeptide, analog or derivative of the present invention are also encompassed within the present invention, and can be generated by known techniques. Such fragments include but are not limited to F(ab')$_2$ fragments which can be generated by pepsin digestion of an intact antibody molecule, and Fab fragments which can be generated by reducing the disulfide bridges of the F(ab')$_2$ fragments. Alternatively, Fab expression libraries can be constructed (Huse, et al., 1989, Science 246: 1275–1281) to allow rapid identification of Fab fragments having the desired specificity to the PauA polypeptide, analog or derivative.

Techniques for the production of monoclonal antibodies and antibody fragments are well-known in the art, and are additionally described, among other places, in Harlow and Lane, 1988, *Antibodies: A Laboratory Manual*, Cold Spring Harbor Laboratory; and in J. W. Goding, 1986, *Monoclonal Antibodies: Principles and Practice*, Academic Press, London. All of the above-cited publications are incorporated herein by reference.

5.6. Anti-Sense Oligonucleotides and Ribozymes

Also within the scope of the present invention are oligonucleotide sequences that include anti-sense oligonucleotides, phosphorothioates and ribozymes that function to bind to, degrade and/or inhibit the translation of pauA mRNA.

Anti-sense oligonucleotides, including anti-sense RNA molecules and anti-sense DNA molecules, act to directly block the translation of mRNA by binding to targeted mRNA and preventing protein translation. For example, antisense oligonucleotides of at least about 15 bases and complementary to unique regions of the DNA sequence encoding a PauA polypeptide can be synthesized, e.g., by conventional phosphodiester techniques.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hammerhead motif ribozyme molecules that specifically and efficiently catalyze endonucleolytic cleavage of pauA mRNA sequences are also within the scope of the present invention.

Specific ribozyme cleavage sites within any potential RNA target are initially identified by scanning the target molecule for ribozyme cleavage sites which include the following sequences, GUA, GUU, and GUC. Once identified, short RNA sequences of between about 15 and 20 ribonucleotides corresponding to the region of the target gene containing the cleavage site can be evaluated for predicted structural features such as secondary structure that may render the oligonucleotide sequence unsuitable. The suitability of candidate targets can also be evaluated by testing their accessibility to hybridization with complementary oligonucleotides, using, e.g., ribonuclease protection assays.

Both the anti-sense oligonucleotides and ribozymes of the present invention can be prepared by known methods. These include techniques for chemical synthesis such as, e.g., by solid phase phosphoamite chemical synthesis. Alternatively, anti-sense RNA molecules can be generated by in vitro or in vivo transcription of DNA sequences encoding the RNA molecule. Such DNA sequences can be incorporated into a wide variety of vectors which incorporate suitable RNA polymerase promoters such as the T7 or SP6 polymerase promoters.

Various modifications to the oligonucleotides of the present invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

5.7. Diagnostic Kits

The present invention further provides diagnostic kits. In a non-limiting embodiment, the diagnostic kit comprises a first container comprising a PauA protein, substantially homologous polypeptide, peptide fragment, fusion protein, analog, or derivative of the present invention that specifically binds to antibodies that are directed against a native PauA protein; and a second container comprising a secondary antibody directed against the anti-PauA protein-specific antibodies. The secondary antibody preferably comprises a detectable label. Such diagnostic kit is useful to detect mammals that are presently, or have previously been, infected with a PauA-producing organism such as *S. uberis*, or that have seroconverted after having been vaccinated with a vaccine of the present invention.

In a further non-limiting embodiment, the diagnostic kit of the present invention comprises a first container comprising an antibody (primary antibody) of the present invention that specifically binds to a native PauA protein; and a second container comprising a secondary antibody that specifically binds to a different epitope on the native PauA protein, or that specifically binds to the primary antibody. The secondary antibody preferably comprises a detectable label. In a further non-limiting embodiment, the diagnostic kit comprises a container comprising a polynucleotide molecule or oligonucleotide molecule of the present invention that is useful to specifically amplify a PauA protein-encoding polynucleotide molecule of a pathogen such as *S. uberis*. These latter two diagnostic kits are useful to detect animals presently infected with a PauA-producing organism such as *S. uberis*.

The following examples are illustrative only, and are not intended to limit the scope of the present invention.

6. EXAMPLE

Identification and Cloning of DNA Molecules Encoding PauA

6.1. Amino Acid Sequence Analysis

A PauA protein from *S. uberis* strain c216 (Lot No. 053196w) was purified using techniques described in International Patent Publication WO 93/14209, i.e., by ammonium sulfate precipitation from a cell-free culture filtrate followed by size-exclusion chromatography, then separated on a 16% SDS-PAGE gel (Novex, San Diego, Calif.), and electroblotted to ProBlott (Applied Biosystems, Foster City, Calif.) for N-terminal Edman sequencing. The region of the blot corresponding to the PauA band (ca. 35 kDa) was excised and subjected to amino acid sequence analysis in an ABI 494 protein sequencer (Applied Biosystems). For internal sequencing, purified PauA was separated on a 16% SDS-PAGE gel, as above, and stained with a modified silver stain (Shevchenko, et al., 1996, Anal. Chem. 68:850–858). The PauA band was excised and the gel slice was reduced with DTT, alkylated with acrylamide, then washed in 50% acetonitrile/$NH_4HCO_3$, and dried in vacuo. The gel slice was treated with 0.1 μg of modified trypsin (Promega, Madison, Wis.) in a 50 μl volume, and incubated at 37° C. overnight. The peptides from the tryptic cleavages were extracted twice by sonication in 150 μl of 60% acetonitrile/ $NH_4HCO_3$ prior to separation by RP-HPLC on a 1×250 mm Vydac $C_{18}$ column (Nest Group, Inc., Southboro, Mass.). Peptide peaks absorbing at 220 nm were collected and subjected to analysis on an ABI 494 protein sequencer. The amino acid sequences obtained are presented as SEQ ID NOS:5–12. Pep-1 (SEQ ID NO:5) and Pep-2 (SEQ ID NO:6) were obtained following N-terminal sequencing, while Pep-3 through Pep-8 (SEQ ID NOS:7–12) resulted from enzymatic trypsin treatment of purified PauA.

6.2. Isolation Of Chromosomal DNA from *S. uberis*

*S. uberis* strains c216 and 95–140 were incubated separately in 100 ml static brain heart infusion broth (BHI, Difco, Detroit. Mich.) at 37° C. for 24 hr and then harvested (7,700×g, 20 min). The wet cell pellet was stored at −20° C. until use. Cells were washed by resuspension of the wet cell pellet in 5 ml Tris-HCl (10 mM)/EDTA (1 mM) (TE), harvested (2,000×g, 15 min), and resuspended in 2 ml TE. The washed cells were heat-treated at 65° C. for 20 min, frozen at −20° C. overnight, then lysed by addition of 250 U mutanolysin (Sigma), 100 mg lysozyme (Sigma), and 50 μg RNAse A (Sigma) and incubation at 37° C. for 105 min. Proteinase K (500 μg) (Sigma) was added, and the incubation was continued for an additional 3 hrs prior to the addition of SDS to a final concentration of 2% (w/v) to complete lysis. The lysed cells were incubated at 37° C. for an additional 30 min, extracted once with Tris-saturated phenol, and extracted twice with phenol/chloroform/isoamyl alcohol (25:24:1). Chromosomal DNA was precipitated by addition of 2.5 volumes of absolute ethanol and 0.1 volume 3 M NaAc, pH 5.2, incubated at −20° C. for 24 hr, and pelleted by centrifugation (15,000×g, 15 min, 4° C.). The DNA was rinsed with 70% ethanol, dried, resuspended in TE, and quantitated by absorbance at 260 nm.

6.3. Partial Cloning of a PauA Gene from *S. uberis*

Degenerate oligonucleotides (FIG. 1) were designed based on the amino acid sequencing of purified *S. uberis* PauA. Oligonucleotide RA9 (SEQ ID NO:14) was designed to hybridize to the portion of the pauA gene encoding amino acids 11–18 of Pep-1 (SEQ ID NO:5). Oligonucleotides ER35 (SEQ ID NO:15) and ER36 (SEQ ID NO:16) were designed to hybridize to the portion of the pauA gene encoding amino acids 13→5 of the internal Pep-5-sequence (SEQ ID NO:9), and differ in their levels of degeneracy.

For PCR amplification of a fragment of the pauA gene, oligonucleotide RA9 (SEQ ID NO:14) was used either alone or in combination with ER35 (SEQ ID NO:15) or ER36 (SEQ ID NO:16) in 50 μl reactions containing 1×PC2 buffer (Ab Peptides, Inc., St. Louis, Mo.), 200 μM of each deoxy-NTP, 100 pMol of each primer, 7.5 U KlenTaq1 (Ab Peptides), and 0.15 U cloned Pfu (Stratagene, La Jolla, Calif.) thermostable polymerases. The DNA template was 500 ng purified chromosomal DNA from *S. uberis* strain c216 or strain 95–140. Amplification was carried out as follows: denaturation (94° C. for 5 min); 30 cycles of denaturation (95° C. for 30 sec), annealing (60° C. for 1 min), and polymerization (72° C. for 2 min); followed by a final extension at 72° C. for 7 min.

The amplified products were visualized by separation on a 2% (w/v) NuSieve GTG agarose gel (FMC Bioproducts, Rockland, Me.). Reactions employing RA9 (SEQ ID NO:14) alone with DNA from *S. uberis* strain c216 as the template resulted in amplification of a distinct 640 bp product. When RA9 (SEQ ID NO:14) was combined with oligonucleotide ER35 (SEQ ID NO:15) or ER36 (SEQ ID NO:16) in PCR reactions using chromosomal DNA from either *S. uberis* strain c216 or strain 95–140 as the template, two products of 640 bp and 560 bp were routinely amplified. This data suggested that the degenerate oligonucleotide RA9 (SEQ ID NO:14) was capable of binding within the pauA region, and that its binding location was towards the C-terminal side of Pep-5 (SEQ ID NO:9), the target binding region of ER35 (SEQ ID NO:15) and ER36 (SEQ ID NO:16).

The PCR products resulting from reactions employing DNA from *S. uberis* strain c216 and RA9 (SEQ ID NO:14) (640 bp), or RA9 (SEQ ID NO:14) plus ER35 (SEQ ID NO:15) (640 and 560 bp), were further analyzed. PCR reaction products obtained following amplification of DNA from *S. uberis* strain 95–140 with the primer pair RA9/ER35 (640 and 560 bp) were also analyzed to determine whether the pauA regions from these strains were similar. The 640 bp and 560 bp products from *S. uberis* strain c216, and the 640 bp product from *S. uberis* strain 95–140 were separately cloned into pUC18 following digestion of the PCR products with the appropriate restriction endonucleases (KpnI (RA9) or KpnI plus BamHI (RA9/ER35)). Sequence analysis of the resulting plasmids confirmed that the secondary binding site for RA9 (SEQ ID NO:14) was located 3' distal to the binding site for oligonucleotide ER35 (SEQ ID NO:15) (which was at amino acids 13→5 of the internal Pep-5 (SEQ ID NO:9)). Additionally, comparison of a 360 nucleotide region within the 640 bp DNA fragments amplified from *S. uberis* strain c216 and strain 95–140 indicated that a very high (99.2%) nucleotide identity exists between the partial pauA genes from these two strains. Inspection of the sequence indicated the presence of restriction endonuclease sites for EcoRI, HindIII, SpeI, and SalI within the pauA ORF, thereby precluding the use of these enzymes during construction of plasmid genomic libraries designed to obtain the entire pauA region localized to a unique restriction fragment.

6.4. Construction and Screening of Plasmid Genomic Libraries

Ten μg of chromosomal DNA from *S. uberis* strain c216 and from strain 95–140 were separately digested with restriction endonuclease BglII at 37° C. for 8 hr, extracted with phenol/chloroform (24:1), and stored at −20° C. One μg of plasmid vector DNA (pUC18) was prepared by digestion with BamHI and dephosphorylated using calf intestinal phosphatase as recommended by the supplier (New England Biolabs, Beverly, Mass.). Linear, dephosphorylated vector (0.5 μg) was ligated to 5 μg BglII-digested chromosomal DNA, and used to transform E. coli DH5α cells (Max Efficiency) as recommended by the supplier (Gibco BRL, Gaithersburg, Md.).

A skim-milk agar plate assay was utilized to facilitate detection of PauA activity. For the purpose of library screening in E. coli, the plate assay materials consisted of BHI agar (Difco) supplemented with nonfat dry milk (1% w/v; Oxoid™), bovine plasminogen (0.015 U/ml; Sigma catalog No. P-9156), and ampicillin (100 ug/ml; Sigma). Library screening was also conducted using these plates further supplemented with 0.1 mM IPTG to induce the lactose promoter of pUC18. This plate assay allowed differentiation of non-specific protease activity from plasminogen-dependent PauA activity by omission of plasminogen from control plates. This modification was used to confirm plasminogen-dependent clearing of skim-milk for putative positive clones obtained through library screening.

Isolates of transformed E. coli strain DH5a that produced zones of clearing on the above-described skim-milk plates were chosen for further analysis. FIG. 2 shows an example of one such isolate transformed with DNA from S. uberis strain 95–140. One isolate containing DNA from S. uberis strain c216 and one isolate containing DNA from S. uberis strain 95–140 DNA were selected, clonally purified, and their ability to express plasminogen-dependent PauA activity was confirmed by their inability to produce a zone of clearing following growth of individual colonies on plasminogen-free skim-milk plates. Plasminogen dependence was confirmed by growth of each isolate in Luria broth (Difco) containing ampicillin (100 μg/ml), followed by spotting aliquots of unfiltered culture supernate onto Todd-Hewitt agar (Becton-Dickinson and Co., Cockeysville, Md.) supplemented with skim-milk (1% w/v) in the presence or absence of 0.015 U/ml bovine plasminogen. These isolates were designated as strain Pz318, which expresses PauA from S. uberis strain c216; and strain Pz319, which expresses PauA from S. uberis strain 95–140; their respective plasmids were designated pER318 and pER319.

6.5. Preliminary Analysis of the PauA Coding Region

Based on nucleotide sequence analysis of the PCR-amplified internal 640 bp DNA fragment corresponding to a portion of the gene encoding PauA from S. uberis strain c216, the identity of the inserts in the plasmids obtained by library screening were confirmed by PCR. Thus, pER318 and pER319 were used as templates in PCR employing pauA-derived primer RA9 (SEQ ID NO:14), alone or in combination with ER37 (SEQ ID NO:17) or ER40 (SEQ ID NO:19). Fifty μl reaction mixtures contained 1×PC2 buffer, 200 μM of each dNTP, 100 pMol of each primer, 7.5 U KlenTaq1 polymerase, and 0.15 U cloned Pfu polymerase. Synthesis was carried out as follows: denaturation (94° C. for 5 min); 30 cycles of denaturation (95° C. for 30 sec), annealing (60° C. for 1 min), and polymerization (72° C. for 2 min); followed by a final extension at 72° C. for 7 min. All reactions successfully amplified products corresponding to the expected 640 bp (amplified with RA9), 500 bp (amplified with RA91ER37), and 300 bp (amplified with RA9/ER40), which DNA fragments are predicted by the known partial sequence of the pauA gene. This data strongly suggested that the inserts present within pER318 and pER319 were capable of encoding functionally active PauA.

Plasmids pER318 and pER319 were subjected to automated DNA sequence analysis (ABI Model 377; Applied Biosystems) at the Advanced Genetic Analysis Center, St. Paul, Minn.., to more completely determine the structure of the pauA region in S. uberis strain c216 and strain 95–140, respectively. Oligonucleotides ER40 (SEQ ID NO:19) and ER42 (SEQ ID NO:21) were derived from the previously determined partial pauA nucleotide sequence, and were used to sequence outward from this 640 bp region. When combined with the 640 bp partial gene sequence, this additional sequencing resulted in determination of the preliminary sequence of the entire pauA ORF, as well as regions immediately flanking the cloned pauA gene. Furthermore, vector-specific M13 forward and reverse primers were used to determine the endpoints of the cloned S. uberis DNA regions. Analysis of these sequences indicated that genes encoding proteins with high degrees of homology to Streptococcus pneumoniae HexA and HexB proteins are present within the cloned inserts in pER318 and pER319, as shown in FIG. 3. HexA and HexB proteins are highly conserved with MutS and MutL homologues, respectively, throughout several prokaryotic and eukaryotic genera, including humans. The HexA and HexB proteins play a role in mismatch DNA repair during the process of transformation and DNA replication in S. pneumoniae. Interestingly, Hex A imparts a dominant negative phenotype when overexpressed in E. coli (Prudhomme, et al., 1991, J. Bacteriol. 173:7196–7203), thereby leading to an increased spontaneous mutation rate.

6.6. Specific PCR Amplification of the S. uberis PauA Gene

Results of the preliminary sequencing from both the PCR-amplified 640 bp regions of pauA and the outward sequencing from this region utilizing plasmids pER318 and pER319 were used to design oligonucleotide primers for the specific amplification of the intact pauA gene directly from S. uberis chromosomal DNA. This approach was preferred based on the desire to eliminate the introduction of sequencing errors due to possible mutations arising during the cloning of intact pauA in E. coli. This was of particular concern in view of the known toxicity of other intact streptokinases in E. coli, as reported elsewhere (Estrada, et al., 1992, BioTechnol. 10:1138–1142), and the reported negative dominance (mutator phenotype) exhibited by HexA when expressed in E. coli (Prudhomme, et al., 1991, above).

Accordingly, oligonucleotides ER45 (SEQ ID NO:24) and ER46 (SEQ ID NO:25), which flank the intact pauA gene, were used to specifically amplify the 1.18 kb regions encoding PauA from S. uberis strains c216 and 95–140. PCR amplifications were carried out in triplicate for each strain. Reaction mixtures contained 200 ng of purified chromosomal DNA, 1×PC2 buffer, 200 μM of each dNTP, 100 pMol of primer ER45 (SEQ ID NO:24), 100 pMol of primer ER46 (SEQ ID NO:25), and 7.5 U KlenTaq1 and 0.15 U cloned Pfu thermostable polymerases in a 100 μl final sample volume. Amplification was carried out as follows: denaturation (94° C. for 5 min); 30 cycles of denaturation (95° C. for 30 sec), annealing (50° C. for 1 min), and polymerization (72° C. for 2 min); followed by a final extension at 72° C. for 7 min to complete the amplification of the target intact pauA gene region. Following amplification, equal aliquots (70 μl, 2.8 μg) from each of the triplicate samples were pooled, and the 1.18 kb product was purified by agarose gel electrophoresis and extraction with glassmilk matrix (GeneClean™, Bio101, LaJolla, Calif.), prior to direct sequence analysis using DyeDeoxy termination reactions on an ABI automated DNA sequencer (Lark Technologies Inc., Houston, Tex.). Synthetic oligonucleotide primers AP1 (SEQ ID NO:13), ER37 (SEQ ID NO:17), ER39 (SEQ ID NO:18), ER40 (SEQ ID NO:19), ER41 (SEQ ID NO:20), ER42 (SEQ ID NO:21), ER43 (SEQ ID NO:22), ER45 (SEQ ID NO:24), and ER46 (SEQ ID NO:25) (FIG. 1) were used to sequence both DNA strands of the amplified products from S. uberis strains c216 and 95–140. The nucleotide sequence of the 1.18 kb region from S. uberis strain c216 is presented as SEQ ID NO:1. The nucleotide sequence of the 1.18 kb region from S. uberis strain 95–140 is presented as SEQ ID NO:3.

6.7. Molecular Analysis of the PauA ORF

The pauA ORF of S. uberis strain c216 extends from nucleotide 120 to 980 of SEQ ID NO:1, which encodes a deduced 286 amino acid protein presented as SEQ ID NO:2, that has a theoretical molecular weight of about 33,419 daltons. The pauA ORF of S. uberis strain 95–140 extends from nucleotide 121 to 981 of SEQ ID NO:3, which encodes a different deduced 286 amino acid protein presented as SEQ ID NO:4. Based on N-terminal sequence analysis, amino acids 1–25 of both amino acid sequences appear to be removed during maturation of the native PauA. Consistent with this is the observation that the 25 amino acid peptide (2,767 Da) is hydrophobic and positively charged, which is characteristic of signal sequences (VonHeijm, 1985, J. Mol. Biol. 184: 99–105). A putative bi-directional transcriptional terminator (FIG. 4) is located between the opposing pauA and HexA ORFs at nt 978–1,088 in the strain c216 sequence (SEQ ID NO:1). Regions of inverted symmetry predicted to form the base of this stem-loop structure extend from nucleotides 1,015 to 1,032 and from nucleotides 1,054 to 1,071. In addition, a nearly identical putative bi-directional transcriptional terminator is located between the opposing pauA and HexA ORFs at nt 979–1,089 in the strain 95–140 sequence (SEQ ID NO:3). Regions of inverted symmetry predicted to form the base of this stem-loop structure extend from nucleotides 1,016 to 1,033 and from nucleotides 1,055 to 1,072. The calculated free energy of association for these stem-loop structures in the corresponding mRNA is about −19 kcal (Tinoco, et al., 1973, Nature New Biol. 246:40–41).

Sequence analysis indicates a high degree of nucleotide identity within the region of the 1.18 kb fragment between S. uberis strain c216 and strain 95–140. Differences between nucleotides and encoded amino acids in this region are summarized in TABLE 1 below.

TABLE 1

| DNA bp No. | Strain c216 | Strain 95-140 | Protein AA. No. | Strain c216 | Strain 95-140 |
|---|---|---|---|---|---|
| 120 | —[a] | T | —[b] | — | — |
| 336 | G | A | 73 | D | N |
| 463 | A | G | 115 | Q | R |
| 490 | A | G | 124 | Q | R |
| 751 | T | G | 211 | L | R |
| 838 | A | C | 240 | Q | P |
| 843 | C | G | 242 | H | D |
| 896 | A | G | — | — | — |
| 982 | G | T | — | — | — |
| 1043 | C | A | — | — | — |
| 1090 | G | A | — | — | — |

[a]A single base insertion/deletion is present immediately upstream of the pauA ATG start codon.
[b]The nucleotide change is silent or is not present within a putative ORF.

7. EXAMPLE

Expression of Recombinant PauA in E. coli

7.1. Construction of Expression Plasmids

Oligonucleotide primers ER43 (SEQ ID NO:22) and ER45 (SEQ ID NO:24) (FIG. 1) were designed to specifically amplify the entire nucleotide sequence encoding the full-length PauA protein from S. uberis strain 95–140. This sequence also includes the natural putative transcriptional terminator region described in Section 6.7 above, and a small 3' portion of the HexA gene (SEQ ID NO.3, nt 121–1,181). Additionally, primers ER44 (SEQ ID NO:23) and ER45 (SEQ ID NO:24) were used to specifically amplify a 5' truncated portion of the pauA gene which lacks the putative encoded signal sequence (amino acids 1–25). This truncated DNA fragment contains the common 3' region, extending from nt 196–1,181, but is predicted to encoded a cytoplasmically localized PauA protein following expression in E. coli. PCR amplification was carried out in triplicate using 200 ng of purified chromosomal DNA from S. uberis strain 95–140 in each 100 μl reaction. Samples also contained 1×PC2 buffer, 200 μM of each dNTP, 100 pMol of each primer, 7.5 U KlenTaq1 polymerase and 0.15 U cloned Pfu polymerase. Amplification conditions were as follows: denaturation (94° C. for 5 min); 30 cycles of denaturation (95° C. for 30 sec), annealing (50° C. for 1 min), and polymerization (72° C. for 2 min); followed by a final extension at 72° C. for 7 min.

Following amplification with either ER43 (SEQ ID NO:22) plus ER45 (SEQ ID NO:24), or ER44 (SEQ ID NO:23) plus ER45 (SEQ ID NO:24), the triplicate samples were separately pooled by combining 7 μl of each reaction mixture to produce a final volume of 21 μl. The synthetic DNA fragments were separated in 1% (w/v) agarose and the 1,001 bp (ER44/ER45) and 1,073 bp (ER43/ER45) products were purified (JetSorb™, GenoMed, Research Triangle Park, N.C.). Following digestion of the purified DNA with KpnI and XbaI, approximately 0.3 μg of the fragments were ligated to 0.5 μg of KpnI plus XbaI restricted, dephosphorylated pEA181 vector DNA. Recombinant plasmids were transformed into competent E. coli TAP56 cells (Pfizer in-house strain) by the method of Hanahan (1983, J. Mol. Biol. 166: 557). Cells were grown in 1 ml SOC medium (Gibco BRL) for 75 min at 30° C. Transformants were grown and maintained at ≦30° C. to prevent induction of the $P_L$ promoter resulting from inactivation of the temperature-sensitive cI857 repressor. Two strains isolated in this manner were retained for expression of recombinant PauA. Strain Pz330 harbors plasmid pER330, which expresses the full-length pauA gene resulting from amplification of chromosomal DNA with primers ER43/ER45. Strain Pz332 harbors plasmid pER332, which expresses the truncated (signal peptide-deleted) pauA gene resulting from amplification with primers ER44/ER45.

As an additional example, the PCR products resulting from amplification of chromosomal DNA from S. uberis strain 95–140 employing primers ER43/ER45 or ER44/ER45, were cloned in-frame with the lacZα peptide of pUC19 following digestion with PstI plus XbaI. The resulting plasmids, designated as pER326 and pER328, encode full-length and truncated (signal peptide-deleted) PauA, respectively, and were introduced into E. coli DH5α to give strains Pz326 and Pz328, respectively.

7.2. Expression of Recombinant PauA (rPauA)

The four strains described above in Section 7.1 were tested for their ability to express either full-length recombinant PauA protein (rPauA) (i.e., with signal sequence) (Pz326, Pz330), or rPauA with the signal sequence deleted (Pz328, Pz332). Overnight starter cultures of each strain were grown in shake flasks in Luria broth containing ampicillin (100 mg/L) or kanamycin (50 mg/L), then diluted 1:10 into fresh growth media. Following a period of 4–6 hr, cultures were induced either by addition of 0.5 mM IPTG (Pz326, Pz328), or by a temperature shift from 30° to 42° C. (Pz330, Pz332). Induction of recombinant protein expression was carried out for 2 hr prior to cell harvest. Whole cell pellets were collected, resuspended in Laemmli lysis buffer, and the lysate analyzed by SDS-PAGE and Western blot. A cell pellet of S. uberis strain 95–140 was similarly obtained after 22 hrs of growth in BHI broth culture and analyzed by Western blot for comparison.

Pre-induced and induced whole cell pellet samples were separated on 14% polyacrylamide gels and either stained with Coomassie brilliant blue (FIG. 5), or Western blotted with murine monoclonal antibody EC-3 raised against native PauA from S. uberis strain c216 (FIG. 6) (see WO 93/14209 for details regarding Mab EC-3). Although the example shown is not optimized for expression, significant production of both full-length and signal sequence-deleted rPauA was obtained using transformed E. coli strains Pz330 and Pz332, respectively, following induction at 42° C. A small proportion of processed rPauA was detected in strain Pz330 (FIG. 6, lane 7), suggesting that the heterologous signal sequence of S. uberis pauA is recognized and processed by the E. coli secretion apparatus. However, induction of recombinant protein expression in Pz330 was detrimental to cell growth, suggesting that over-expression of full-length rPauA may interfere with normal export processes in the heterologous E. coli host.

7.3. Enzymatic Activity of rPauA

The activity of rPauA was determined using a chromogenic assay which measures activation of bovine plasminogen, as described below. Aliquots of whole cell pellets from the above-described E. coli cultures (Pz326, Pz328, Pz330, Pz332) and from S. uberis strain 95–140 were analyzed. Activity was consistent with the relative amount of recombinant protein expressed in the heterologous host. Maximal titer was obtained for strain Pz332 (TABLE 2).

TABLE 2

| Strain | $OD_{650}{}^a$ | Titer[b] |
|---|---|---|
| S. uberiss 95-140 | 0.274 | 1.0 |
| Pz326 | 0.811 | 23.3 |
| Pz328 | 0.579 | 5.3 |
| Pz330 | 0.240 | 1.0 |
| Pz332 | 0.396 | >128 |

[a]Optical density of first dilution of sample in ELISA plate.
[b]Titer calculated as described in text.

The chromogenic assay was carried out as follows. Buffer reagents for the chromogenic assay consisted of TT buffer (0.1% Tween 80, 50 mM Tris-HCl, pH 8.0), and NaT buffer (1.77 M NaCl, 52 mM Tris-HCl, pH 7.0). These buffers are stable at room temperature and may be stored up to one month prior to use. A working stock of urokinase (Sigma catalog No. U-8627) was prepared by rehydration in water and stored at −70° C. The concentration of the frozen working stock was 0.51 U/ml, and was diluted 1:10 using TT buffer for a starting concentration of 0.051 U/ml. Bovine plasminogen (Sigma catalog No. P-9156) was hydrated with Super Q $H_2O$ to 1.5 U/ml and stored at −70° C. Substrates included D-Ile-Phe-Lys p-nitroanilide (Sigma catalog No. I6886), and D-Val-Leu-Lys p-nitroanilide (Sigma catalog No. V-0882; Fluka catalog No. 94680, Fluka Chemical Corp., Ronkonkoma, N.Y.). Working stock solutions of these substrates were prepared by rehydration to 1 mg/ml in water and stored at −70° C.

Immulon 2 assay plates (Dynatech Laboratories, Inc., Chantilly, Va.) were prepared as follows. TT buffer (20 μl) and bovine plasminogen (20 μl) were prealiquoted to Immulon 2 plates. In a V-Bottom plate (Dynatech Laboratories, Inc.), TT buffer (50 μl/well) was added to rows B–H. The media control, positive control, and samples were added to row A. The samples, media control, and positive control were all run in duplicate wells. To the proper well was added either 100 μl of control or 100 μl of sample, which was then serially diluted down the plate, with 50 μl discarded out of the last row. Ten μl from each well of the V-bottomed plate were transferred to the corresponding Immulon 2 plate which contained pre-aliquoted TT buffer and bovine plasminogen. The plates were covered, mixed well, and incubated at 37° C. for 2 hrs to allow activation of bovine plasminogen. An assay control consisted of urokinase-mediated activation of bovine plasminogen.

The substrate (D-Val-Leu-Lys p-nitroanilide or D-Ile-Phe-Lys p-nitroanilide) was warmed to room temperature. The assay substrate was prepared by diluting the stock substrate to 400 μg/ml (1:2.5 diluton) using NaT buffer, and 100 μl/well of this assay substrate solution was added and the plate covered and mixed. The plates were then incubated at 37° C. for two min. Active PauA catalyzes the conversion of plasminogen to plasmin, which in turn cleaves the tripeptide from p-nitroanilide, which is measured at $A_{405}$.

The plates were read using an ELISA plate reader (Molecular Devices Corp., Palo Alto, Calif.) with SoftMax PRO Ver. 1.2.0 software (Molecular Devices Corp.). Assay plate samples were mixed and the spectral absorbance at 405 nm determined. Valid tests indicate a positive control with an $A_{405}$ of between 1.30 and 1.50 O.D.

In order to estimate titer (inverse of the dilution factor), the sample dilution series was graphed using a scatter plot graph of the dilutions in log scale. The point at which the sample crosses the cut-off value based on the positive control was calculated to be the exact titer. To determine the cut-off value, 50% of the mean O.D. of the positive control (0.051 U/ml) was used. For example, if a sample crossed the cut-off line at 0.007, its dilution factor would be 1/142.86, and its titer would be expressed as 142.86. Further, if a sample crossed the cut-off line at 0.015, it would have a dilution factor of 1/66.67 and the titer would be 66.67.

8. EXAMPLE

Enzymatic and Immunological Evaluation of PauA Peptide Fragments

8.1. Expression of Recombinant GST-PauA Peptides

Oligonucleotide primers ER74 (SEQ ID NO:26) and ER75 (SEQ ID NO:27) were designed to specifically amplify the pauA gene encoding the region encompassing amino acids 27–286 of the encoded PauA. This region corresponds to amino acids 2–261 of mature (secreted) PauA. PCR synthesis was carried out in duplicate using 250 ng purified S. uberis 95–140 chromosomal DNA in each 100 μl reaction. Samples also contained 1×PC2 buffer, 200 μM each dNTP, 100 pMol each primer, 7.5 U KlenTaq1 polymerase and 0.15 U cloned Pfu polymerase. Amplification conditions were: denaturation (94° C., 5 min); 30 cycles of denaturation (95° C., 30 sec), annealing (60° C., 30 sec), and polymerization (72° C., 1 min); followed by a final extension at 72° C., for 7 min. Following amplification, both samples were combined and the 815 bp fragment purified (QiaQuick™ kit, Qiagen, Santa Clarita, Calif.). Following digestion of the purified DNA with XhoI and NotI, the fragment was cloned into pGEX5x-2 or pGEX5x-3 vector DNA (Pharmacia Biotech Inc., Piscataway, N.J.). The resulting recombinant plasmids, pER354 and pER355, respectively, contained the region encoding amino acids 27–286 of encoded PauA of *S. uberis* 95–140 (see SEQ ID NO:4) placed out of phase with the N-terminally encoded glutathione S-transferase (GST) of the expression vector.

Plasmid pER354 was modified to delete COOH-terminal regions of mature PauA while also restoring the frame at the fusion point with the vector encoded GST sequence. Plasmids which produce either mature or N-terminal fragments of mature PauA (i.e., carboxyl deletions) were constructed by first repairing the frame at the GST-PauA fusion point by digestion of pER354 with XmaI and AgeI to produce pER356. This plasmid expresses a 26 kDa GST peptide translationally fused to amino acids 28–286 of encoded PauA, and its product is referred to as mature PauA. COOH-terminal deletions of mature PauA were generated by further treatment of this plasmid with either SpeI, NruI, or HindIII followed by digestion with NotI. After treatment with Klenow fragment where appropriate to create blunt ends, the plasmids were religated to create plasmids pER363, pER364, and pER365, respectively. These plasmids express the 26 kDa GST peptide fused to amino acids 28–103, 28–170, and 28–208, respectively, of encoded PauA, as presented in TABLE 3.

Plasmid pER355 was further modified to delete either $NH_2$— or COOH-terminal regions of PauA, while also restoring the frame at the fusion point with the vector-encoded GST sequence. $NH_2$-terminal deletions were created by treatment of pER355 with SalI alone, or SmaI plus NruI, followed by religation to repair the GST-PauA fusion junction. The resulting plasmids, pER358 and pER359, express the GST peptide fused to amino acids 104–286 and 172–286, respectively, of encoded PauA. Two plasmids representing internal PauA peptide fragments were subsequently produced by treatment of pER358 with NruI or HindIII followed by digestion with NotI, Klenow treatment, and religation. These recombinant plasmids, pER366 and pER367, express the GST peptide fused to amino acids 104–170 and 104–208 of encoded PauA, respectively. Finally, a plasmid capable of expressing GST fused to a small PauA fragment (amino acids 172–208 of encoded PauA) was created by digestion of pER359 with HindIII plus NotI, followed by Klenow treatment, and religation. This plasmid was named pER368. The encoded fragments and estimated molecular weights for the PauA-specific peptides expressed as fusion proteins with GST are summarized in TABLE 3.

TABLE 3

| Plasmid or Strain[a] | PauA Peptide Fragment[b] | No. amino acids (PauA) | Est'd. mol. weight[c] kDa |
|---|---|---|---|
| pER356 | 28-286 | 259 | 30.5 |
| pER363 | 28-103 | 76 | 8.8 |
| pER364 | 28-170 | 143 | 16.7 |
| pER365 | 28-208 | 181 | 21.1 |
| pER358 | 104-286 | 183 | 21.7 |
| pER359 | 172-286 | 115 | 13.7 |
| pER366 | 104-170 | 67 | 7.9 |
| pER367 | 104-208 | 105 | 12.3 |
| pER368 | 172-208 | 37 | 4.3 |

[a]Strain designations are the same as the plasmid except that Pz replaces PER preceding the plasmid number.
[b]Amino acid numbers correspond to that of encoded PauA protein shown in SEQ ID NO:4.
[c]Molecular weight of the PauA portion of the fusion protein is presented. GST is ~26kDa.

All GST-PauA fusion proteins, except that encoded by pER363, were expressed in *E.coli* and purified by affinity chromatography as recommended by the manufacturer (Pharmacia). Since expression of the protein encoded by pER363 led to inclusion body formation in *E.coli*, these protein aggregates were purified following cell lysis with lysozyme. Cells were incubated on ice for 10 min prior to addition of 10 vol 2×RIPA/TET (5:4 v/v). 2×RIPA contains 20 mM Tris (pH 7.4), 0.3 M NaCl, 2% sodium deoxycholate, and 2% (v/v) Igepal CA-630. TET buffer contains 0.1 M Tris (pH 8.0), 50 mM EDTA, and 2% (v/v) Triton X-100. The suspended cell mixture was vortexed and incubated on ice for 5 min, then sonicated until the suspension was no longer viscous. Inclusion bodies were harvested by centrifugation (15,000×g, 20 min), resuspended in $H_2O$, and stored at −80° C.

8.2. Production of PauA Fragment by Proteolytic Cleavage

Approximately 13 ml of native PauA (Lot No. 9700710A) purified from *S. uberis* strain 95–140 at 0.55 mg/ml was dialyzed against 50 mM Tris, pH 8.8 at 4° C. The retentate was concentrated to ~2.5 ml using a YM10 membrane and a stirred cell. Final protein concentration was 2.64 mg/ml. This concentrate was treated with 120 U of thrombin (Boehringer Ingelheim) for 3 days at rm temp, and the digest was frozen at −20° C. Purification of an ~16 kDa fragment from the digest was accomplished with a Superdex 75 column (16/60) (Pharmacia) on which 2 ml of the digest was applied. Appropriate fractions were collected and pooled based on SDS-PAGE analysis. The final protein concentration was 0.165 mg/ml in 2.5 ml. N-terminal sequencing confirmed that the 16 kDa peptide represented a portion of the carboxyl terminal half of PauA. The sequence obtained (KRVEEPITHP) (SEQ ID NO:28) began at lysine 149 of encoded PauA of *S. uberis* strain 95–140. Accordingly, this proteolytically-derived peptide is referred to as $PauA^{149-286}$.

8.3. Enzymatic Activity of PauA Peptide Fragments

The enzymatic activities of the nine GST-PauA fusion proteins described in TABLE 3, and the proteolytic PauA fragment ($PauA^{149-286}$) described in Section 8.2 above, were compared to the native PauA using the chromogenic assay essentially as described in Section 7.3 above. The enzymatic activity of the purified $GST-PauA^{28-286}$ fusion protein (titer= 3448) was similar to that of native PauA (titer=3256), while the remaining PauA peptide fragments lacked enzymatic activity. The PauA specific activity was calculated by dividing-the titer by the amount of PauA specific protein present in the purified protein preparation. When this correction was performed, the specific activity for native PauA was 5.9 chromogenic units/$\mu$g and the specific activity of $GST-PauA^{28-286}$ was 1.4. This data suggests that although recombinantly produced GST-PauA is somewhat less active enzymatically than purified native PauA, it does exhibit significant enzymatic activity.

8.4. Characterization of Immune Responses in Mice

8.4.1. Immunization of Mice with PauA Peptide Fragments

A murine model for vaccination was utilized to evaluate the immunogenicity of the PauA peptide fragments prepared as described above. Briefly, experimental groups consisting of 10 female Balb/c mice (16–18 g) were immunized at days 0, 21, and 42. Blood samples were obtained on experimental days 0, 21, 35 and 56. Sera from these samples were pooled by experimental group and analyzed by ELISA reactivity to solid phase native purified PauA, and serum neutralization of native purified PauA chromogenic activitity.

Formulation of the native PauA and the various peptide fragments was in a squalene-in-water emulsion vehicle containing Quil A (Superfos) as an immunostimulant at a level-which was non-toxic for mice. Proteins were formulated at 3–5 μg in a 100 ;if dose and administered subcutaneously. The control non-antigen vaccine consisted of Dulbecco's PBS (DPBS; Gibco-BRL) containing the vehicle/ immunostimulant without an antigenic component.

8.4.2. Immunogenicity of PauA Peptide Fragments

The various murine sera obtained from the above immunization studies were analyzed to determine whether PauA-specific antibodies were generated, and to determine the nature of the generated antibodies. A PauA-specific IgG ELISA was utilized to determine the specificity of sera following immunization with the proteolytic PauA fragment (PauA$^{149-286}$) and each of the GST-PauA fusion proteins. One hundred μl of purified native PauA (described in International Patent Publication WO 93/14209. and designated therein as "streptokinase") (1.8 mg/ml in PBS) was added to each well of an Immulon II plate (Dynatech) and incubated at 4° C. overnight. The plate contents were decanted and the plate was blotted dry. The plate was blocked by addition to each well of 250 μl 1% Poly(vinyl alcohol) (87–89% hydrolyzed; Aldrich Chemical Company, Inc., Milwaukee, Wis.) in PBS (1% PVA/PBS), and incubation at 37° C. for 1 hr. The plate was decanted again and blotted dry.

The experimental sera were diluted 1:100 in 1% PVA/ PBS, then three-fold serially diluted leaving 100 μl in the sample wells. The positive control was PauA-specific monoclonal antibody, EC-3, which antibody was affinity-purified using immobilized Protein G. This monoclonal antibody was diluted to 2 μg/ml in 1% PVA/PBS, then 100 μl was added to the appropriate wells. A negative control consisted of pooled, pre-vaccinated mouse sera diluted 1:100 in 1% PVA/PBS. One hundred μl of negative control sera was added to the appropriate wells.

Following addition of the experimental and control samples, plates were gently tapped to mix, then placed at 37° C. for 1 hr. Sample wells were washed 5× with 0.05% Tween 20/PBS using an automated microplate washer (model EL403; BIO-TEK Instruments, Inc., Winooski, Vt.). Detection of bound antibodies was by addition of 100 μl conjugated goat anti-mouse IgG (H&L chains, 1.0 mg/ml, Kirkegaard & Perry Laboratories, Gaithersburg, Md.) diluted 1:10, 000 in 1% PVA/PBS. Plates were tapped gently to mix, placed at 37° C. for 1 hr, and washed as previously described. One hundred μl of ABTS (Kirkegaard & Perry) was added to the plate prior to development at rm temp for 15 min. Plates were read at 405/490 nm using a Thermo Max plate reader (Molecular Devices Corp.) and SoftMax PRO Ver. 1.2 program (Molecular Devices Corp.). The IgG ELISA titer was calculated as the inverse of the dilution which gave 50% of the OD$_{405/490}$ of the positive control.

As shown in TABLE 4, immunization of mice with each of the nine GST-PauA fusion proteins resulted in generation of PauA-specific immunoglobulin G. Immunization with either GST-PauA$^{28-286}$, GST-PauA$^{104-286}$, or GST-PauA$^{28-170}$ induced IgG ELISA titers which were equivalent to or greater than that induced by the native PauA. The proteolytically-derived peptide, PauA$^{149-286}$, generated a relatively low titer compared to the recombinant PauA peptide fragments. Following the third immunization, this peptide fragment induced a PauA-specific titer approximately one-tenth that of its most similar comparator peptide, i.e., GST-PauA$^{172-286}$. Although this particular peptide (PauA$^{149-286}$) induced a low IgG response, it is expected that other fragments of native PauA would be capable of eliciting comparable immune responses as shown for the recombinant peptides.

8.4.3. Serum Neutralization Activity

The sera from the above immunizations were further analyzed to determine whether they contained antibodies capable of blocking the conversion of bovine plasminogen to plasmin by PauA. The serum neutralization assay was carried out by dilution of serum samples 1:50 in TEA buffer containing 10% fetal bovine serum (TEA/FBS; Novatech Inc., Grand Island, Nebr.). One liter TEA buffer consisted of 3.34 g Tris Base, 3.54 g Tris HCl, 5.8 g NaCl, 1.1 g EDTA (tetrasodium hydrate), 42.2 g (L)-arginine hydrochloride, and 1.0 ml Tween 80. The buffer pH was adjusted to 8.0, then stored at rm temp until use. FBS was added to TEA buffer just prior to use in the neutralization assay. Serum samples in TEA/FBS were then serially diluted two-fold in TEA/FBS in a V-bottom plate (Dynatech). Twenty-five μl of the test samples were then transferred to an Immulon II plate (Dynatech). Purfied native PauA isolated from *S. uberis* (lot. No. 9700710A) was diluted to 76 μg/ml in TEA Buffer, then 25 μl was added to each well containing pre-aliquoted sera. The plates were gently tapped to mix and placed at 37° C. for 1 hr. The positive control was a lyophilized IgG fraction from a seropositive cow. This IgG fraction was rehydrated to 3.8 mg/ml, diluted 1:50 in TEA/FBS, and transferred to an Immulon II plate. Twenty-five μl of the positive control and 25 μl of FBS. diluted 1:50 in TEA/FBS were aliquoted to the appropriate wells.

Neutralization of PauA activity was detected by addition of substrate. The substrate was prepared by mixing plasminogen (1 U/ml; P-9156, Sigma), Chromozym (1 mg/ml; Boeringer Mannheim, Indianapolis, Ind.), and TEA buffer at a ratio of 2:3:1. One hundred-fifty μl of this substrate was added to each sample well, the plate was tapped gently to mix and then incubated at 37° C. for 90 min. Plates were read at 405/490 nm using a Thermo, Max plate reader and SoftMax PRO Version 1.2 computer program. The titer was calculated as the inverse of the dilution that was equivalent to 50% of the negative control.

The neutralization assay indicated that several peptide fragments were capable of eliciting neutralizing responses directed toward native PauA. Sera obtained following injection of mice with recombinant proteins GST-PauA$^{28-286}$, GST-PauA$^{104-286}$, GST-PauA$^{28-170}$, or GST-PauA$^{28208}$ exhibited neutralizing titers similar to sera obtained from mice injected with the native PauA. Therefore, when injected into mice, these peptide fragments induced the generation of antibodies capable of interfering with the enzymatic activity of purified native PauA.

TABLE 4

| Group[a] | IgG ELISA | | | | Neutralization Assay | | | |
|---|---|---|---|---|---|---|---|---|
| | Day 0 | Day 21 | Day 35 | Day 56 | Day 0 | Day 21 | Day 35 | Day 56 |
| Experiment-1 | | | | | | | | |
| GST-PauA[28-286] | <100 | 135 | 18519 | 43478 | <50 | <50 | 243 | 357 |
| GST-PauA[104-286] | <100 | <100 | 3333 | 25000 | <50 | <50 | <50 | 77 |
| GST-PauA[172-286] | <100 | <100 | 465 | 3226 | <50 | <50 | <50 | <50 |
| GST-PauA[28-170] | <100 | 143 | 11236 | 20833 | <50 | <50 | 58 | 200 |
| GST-PauA[104-170] | <100 | <100 | <100 | 571 | <50 | <50 | <50 | <50 |
| GST-PauA[104-208] | <100 | <100 | 625 | 2083 | <50 | <50 | <50 | <50 |
| GST-PauA[172-208] | <100 | <100 | 250 | 1053 | <50 | <50 | <50 | <50 |
| Native PauA | <100 | <100 | 9091 | 23810 | <50 | <50 | 77 | 244 |
| Experiment-2 | | | | | | | | |
| GST-PauA[28-103] | <100 | <100 | 345 | 1724 | <50 | <50 | <50 | <50 |
| GST-PauA[28-208] | <100 | <100 | 10870 | 9091 | <50 | <50 | 91 | 294 |
| Native PauA | <100 | <100 | 12500 | 26667 | <50 | <50 | 67 | 500 |
| Experiment-3 | | | | | | | | |
| Proteolized PauA[149-286] | <100 | <100 | <100 | 303 | <50 | <50 | <50 | <50 |
| Native PauA | <100 | <100 | 20000 | 20833 | <50 | <50 | <50 | 115 |
| GST Control | <100 | <100 | <100 | <100 | <50 | <50 | <50 | <50 |
| DPBS (Adjuvant Control) | <100 | <100 | <100 | <100 | <50 | <50 | <50 | <50 |

[a]Data is summarized from three different studies and is grouped according to study.
Two controls (GST and DPBS) were included in each experiment and are listed at the bottom of the Table.

All patents, patent applications, and publications cited above are incorporated herein by reference in their entirety.

The present invention is not to be limited in scope by the specific embodiments described, which are intended as single illustrations of individual aspects of the invention. Functionally equivalent compositions and methods are within the scope of the present invention.

What is claimed is:

1. An isolated polynucleotide molecule, comprising a nucleotide sequence encoding a protein comprising the amino acid sequence from amino acid position 26 to amino acid position 286 of SEQ ID NO:2 or SEQ ID NO:4.

2. The isolated polynucleotide molecule of claim 1, comprising the nucleotide sequence from nucleotide position 195 to nucleotide position 977 of SEQ ID NO:1, or from nucleotide position 196 to nucleotide position 978 of SEQ ID NO:3, respectively.

3. The isolated polynucleotide molecule of claim 1, wherein the protein comprises the amino acid sequence of SEQ ID NO:2 or SEQ ID NO:4.

4. The isolated polynucleotide molecule of claim 3 comprising the nucleotide sequence from nucleotide position 120 to nucleotide position 980 of SEQ ID NO:1, or from nucleotide position 121 to nucleotide position 981 of SEQ ID NO:3, respectively.

5. The isolated polynucleotide molecule of claim 4, comprising the nucleotide sequence of SEQ ID NO:1 or a degenerate variant thereof, or the nucleotide sequence of SEQ ID NO:3 or a degenerate variant thereof, respectively.

6. An isolated polynucleotide molecule that hybridizes to a DNA molecule comprising a nucleotide sequence complementary to the nucleotide sequence from nucleotide position 195 to nucleotide position 447 of SEQ ID NO:1, or from nucleotide position 196 to nucleotide position 448 of SEQ ID NO:3, under conditions of 0.5M NaHPO$_4$, 7% sodium dodecyl sulfate (SDS), 1 mM EDTA at 65° C., and washing in 0.2×SSC/0.1% SDS at 42° C., and which polynucleotide molecule encodes a polypeptide that, when administered to a member of a mammalian species, is capable of inducing the production of antibodies that bind specifically to a protein comprising the amino acid sequence from amino acid position 26 to amino acid position 286 of SEQ ID NO:2 or SEQ ID NO:4.

7. The polynucleotide molecule of claim 6, which hybridizes to a DNA molecule comprising a nucleotide sequence complementary to the nucleotide sequence from nucleotide position 195 to nucleotide position 447 of SEQ ID NO:1, or from nucleotide position 196 to nucleotide position 448 of SEQ ID NO:3, under conditions of 0.5M NaHPO$_4$, 7% SDS, 1 mM EDTA at 65° C., and washing in 0.1×SSC/0.1% SDS at 68° C.

8. An isolated polynucleotide molecule, comprising a nucleotide sequence encoding a peptide fragment of a protein consisting of the amino acid sequence of SEQ ID NO:2 or SEQ ID NO:4, which peptide fragment, when administered to a member of a mammalian species, is capable of inducing the production of antibodies that bind specifically to a protein comprising the amino acid sequence from amino acid position 26 to amino acid position 286 of SEQ ID NO:2 or SEQ ID NO:4.

9. The isolated polynucleotide molecule of claim 8, wherein the amino acid sequence from amino acid position 26 to amino acid position 286 of SEQ ID NO:2 or SEQ ID NO:4 is encoded by the nucleotide sequence from nucleotide position 195 to nucleotide position 977 of SEQ ID NO:1, or from nucleotide position 196 to nucleotide position 978 of SEQ ID NO:3, respectively.

10. The isolated polynucleotide molecule of claim 8, wherein the peptide fragment comprises a sub-sequence of amino acids from SEQ ID NO:2 or SEQ ID NO:4 selected from the group consisting of amino acids at positions 28 to 286, and 28 to 170.

11. An isolated polynucleotide molecule comprising a nucleotide sequence encoding a fusion protein, said fusion protein comprising a fusion partner fused to a protein comprising the amino acid sequence from amino acid position 26 to amino acid position 286 of SEQ ID NO:2 or SEQ ID NO:4.

12. The isolated polynucleotide molecule of claim 11, wherein the fusion protein is selected from the group consisting of a P-galactosidase fusion, trpE fusion, maltose-binding protein fusion, glutathione-S-transferase (GST) fusion, and polyhistidine fusion.

13. The isolated polynucleotide molecule of claim 11, wherein the amino acid sequence of the protein from amino acid position 26 to amino acid position 286 of SEQ ID NO:2 or SEQ ID NO:4 is encoded by the nucleotide sequence from nucleotide position 195 to nucleotide position 977 of SEQ ID NO:1, or from nucleotide position 196 to nucleotide position 978 of SEQ ID NO:3, respectively.

14. An isolated polynucleotide molecule comprising a nucleotide sequence encoding a fusion protein, said fusion protein comprising a fusion partner fused to a peptide fragment of a protein consisting of the amino acid sequence of SEQ ID NO:2 or SEQ ID NO:4, which peptide fragment, when administered to a member of a mammalian species, is capable of inducing the production of antibodies that bind specifically to a protein comprising the amino acid sequence from amino acid position 26 to amino acid position 286 of SEQ ID NO:2 or SEQ ID NO:4.

15. The isolated polynucleotide molecule of claim 14, wherein the fusion protein is selected from the group consisting of a P-galactosidase fusion, trpE fusion, maltose-binding protein fusion, glutathione-S-transferase (GST) fusion, and polyhistidine fusion.

16. The isolated polynucleotide molecule of claim 14, wherein the amino acid sequence of amino acid position 26 to amino acid position 286 of SEQ ID NO:2 or SEQ ID NO:4 is encoded by the nucleotide sequence from nucleotide position 195 to nucleotide position 977 of SEQ ID NO:1, or from nucleotide position 196 to nucleotide position 978 of SEQ ID NO:3, respectively.

17. The isolated polynucleotide molecule of claim 14 wherein the peptide fragment comprises a sub-sequence of amino acids from SEQ ID NO:2 or SEQ ID NO:4 selected from the group consisting of amino acids at positions 28 to 286, and 28 to 170.

18. The isolated polynucleotide molecule of claim 17, wherein the fusion partner is GST.

19. A recombinant expression vector, comprising a polynucleotide molecule comprising a nucleotide sequence encoding: (a) a protein comprising the amino acid sequence from amino acid position 26 to amino acid position 286 of SEQ ID NO:2 or SEQ ID NO:4; or (b) a fusion protein comprising a fusion partner fused to the protein of (a); which polynucleotide molecule is in operative association with one or more regulatory elements that control expression of the polynucleotide molecule in a host cell.

20. The recombinant expression vector of claim 19, wherein the amino acid sequence of the protein from amino acid position 26 to amino acid position 286 of SEQ ID NO:2 or SEQ ID NO:4 is encoded by a polynucleotide molecule comprising the nucleotide sequence from nucleotide position 195 to nucleotide position 977 of SEQ ID NO:1, or from nucleotide position 196 to nucleotide position 978 of SEQ ID NO:3, respectively.

21. The recombinant expression vector of claim 19, wherein the fusion protein is selected from the group consisting of a β-galactosidase fusion, trpE fusion, maltose-binding protein fusion, glutathione-S-transferase (GST) fusion, and polyhistidine fusion.

22. The recombinant expression vector of claim 19, further comprising a selectable marker.

23. A recombinant expression vector, comprising a polynucleotide molecule consisting of a nucleotide sequence encoding: (a) a peptide fragment of a protein consisting of the amino acid sequence of SEQ ID NO:2 or SEQ ID NO:4, which peptide fragment, when administered to a member of a mammalian species, is capable of inducing the production of antibodies that bind specifically to a protein comprising the amino acid sequence from amino acid position 26 to amino acid position 286 of SEQ ID NO:2 or SEQ ID NO:4; or (b) a fusion protein comprising a fusion partner fused to the peptide fragment of (a); which polynucleotide molecule is in operative association with one or more regulatory elements that control expression of the polynucleotide molecule in a host cell.

24. The recombinant expression vector of claim 23, wherein the amino acid sequence from amino acid position 26 to amino acid position 286 of SEQ ID NO:2 or SEQ ID NO:4 is encoded by a polynucleotide molecule comprising the nucleotide sequence from nucleotide position 195 to nucleotide position 977 of SEQ ID NO:1, or from nucleotide position 196 to nucleotide position 978 of SEQ ID NO:3, respectively.

25. The recombinant expression vector of claim 23, wherein the peptide fragment comprises a sub-sequence of amino acids from SEQ ID NO:2 or SEQ ID NO:4 selected from the group consisting of amino acids at positions 28 to 286, and 28 to 170.

26. The recombinant expression vector of claim 23, wherein the fusion protein is selected from the group consisting of a β-galactosidase fusion, trpE fusion, maltose-binding protein fusion, glutathione-S-transferase (GST) fusion, and polyhistidine fusion.

27. The recombinant expression vector of claim 23, further comprising a selectable marker.

28. A host cell transformed with the recombinant expression vector of claim 19.

29. A host cell transformed with the recombinant expression vector of claim 23.

30. A method for preparing a polypeptide, comprising culturing a host cell transformed with the recombinant expression vector of claim 19 under conditions conducive to the production of the polypeptide encoded by the expression vector, and recovering the polypeptide from the cell culture.

31. A method for preparing a polypeptide, comprising culturing a host cell transformed with the recombinant expression vector of claim 23 under conditions conducive to the production of the polypeptide encoded by the expression vector, and recovering the polypeptide from the cell culture.

32. A vaccine for protecting a member of a mammalian species against mastitis, comprising an immunologically effective amount of a polynucleotide molecule comprising a nucleotide sequence encoding: (a) a protein comprising the amino acid sequence from amino acid position 26 to amino acid position 286 of SEQ ID NO:2 or SEQ ID NO:4; or (b) a fusion protein comprising a fusion partner fused to the protein of (a); which polynucleotide molecule, or protein or fusion protein encoded thereby, is capable of inducing a protective response against mastitis in the mammal; and a veterinarily acceptable carrier.

33. The vaccine of claim 32 wherein the polynucleotide molecule encoding the amino acid sequence from amino acid position 26 to amino acid position 286 of SEQ ID NO:2 or SEQ ID NO:4 comprises the nucleotide sequence from nucleotide position 195 to nucleotide position 977 of SEQ ID NO:1, or from nucleotide position 196 to nucleotide position 978 of SEQ ID NO:3, respectively.

34. The vaccine of claim 32, comprising a transformed host cell comprising the polynucleotide molecule comprising the nucleotide sequence encoding: (a) a protein comprising the amino acid sequence from amino acid position 26 to amino acid position 286 of SEQ ID NO:2 or SEQ ID NO:4; or (b) a fusion protein comprising a fusion partner fused to the protein of (a); which polynucleotide molecule is expressed in the host cell to produce the protein of (a) or fusion protein of (b).

35. The vaccine of claim 34, wherein the host cell is *E. coli*.

36. A vaccine for protecting a member of species against mastitis, comprising an immunologically effective amount of a polynucleotide molecule comprising a nucleotide sequence encoding: (a) a peptide fragment comprising a sub-sequence of amino acids from SEQ ID NO:2 or SEQ ID NO:4 selected from the group consisting of amino acids at positions. 28 to 286 and 28 to 170; or (b) a fusion protein comprising a fusion partner fused to the peptide fragment of (a); which polynucleotide molecule, or peptide fragment or fusion protein encoded thereby, is capable of inducing a protective response against mastitis in the mammal; and a veterinarily acceptable carrier.

37. The vaccine of claim 36, wherein the polynucleotide molecule encoding the amino acid sequence from amino acid position 26 to amino acid position 286 of SEQ ID NO:2 or SEQ ID NO:4 comprises the nucleotide sequence from nucleotide position 195 to nucleotide position 977 of SEQ ID NO:1, or from nucleotide position 196 to nucleotide position 978 of SEQ ID NO:3, respectively.

38. The vaccine of claim 36, comprising a transformed host cell comprising the polynucleotide molecule comprising the nucleotide sequence encoding the peptide fragment or fusion protein; which polynucleotide molecule is expressed in the host cell to produce the peptide fragment or fusion protein.

39. The vaccine of claim 38, wherein the host cell is *E. coli*.

40. A combination vaccine for protecting a member of a mammalian species against mastitis and one or more diseases or pathological conditions that can afflict the mammal, which combination vaccine comprises an immunologically effective amount of a first component comprising a polynucleotide molecule comprising a nucleotide sequence encoding: (a) a protein comprising the amino acid sequence from amino acid position 26 to amino acid position 286 of SEQ ID NO:2 or SEQ ID NO:4; or (b) a fusion protein comprising a fusion partner fused to the protein of (a); which polynucleotide molecule, or protein or fusion protein encoded thereby, is capable of inducing a protective response against mastitis in the mammal; an immunologically effective amount of a second component comprising an antigen different from the antigen in the first component and capable of inducing a protective response against a disease or pathological condition that can afflict the mammal; and a veterinarily acceptable carrier.

41. The combination vaccine of claim 40, comprising a host cell associated as a pathogen with a disease or pathological condition other than mastitis caused by *S. uberis*, which disease or pathological condition can afflict the mammal, which host cell is transformed with the polynucleotide molecule comprising a nucleotide sequence encoding: (a) a protein comprising the amino acid sequence from amino acid position 26 to amino acid position 286 of SEQ ID NO:2 or SEQ ID NO:4; or (b) a fusion protein comprising a fusion partner fused to the protein of (a); which polynucleotide molecule is expressed in the host cell to produce the protein of (a) or fusion protein of (b), and wherein the host cell is capable of inducing a protective immune response against the disease or pathological condition other than mastitis caused by *S. uberis*.

42. The combination vaccine of claim 41, wherein the host cell is selected from the group consisting of Leptospira spp., Campylobacter spp., Staphylococcus spp., Streptococcus spp., Mycoplasma spp., Klebsiella spp., Salmonella spp., Pasteurella spp., Clostridium spp., *E. coli*, and Neospora spp.

43. The combination vaccine of claim 40, wherein the antigen of the second component of the combination vaccine is capable of inducing a protective response in the mammal against a disease, condition, or pathogen selected from the group consisting of mastitis, bovine herpes virus, bovine respiratory syncitial virus, bovine viral diarrhea virus, parainfluenza virus type I, parainfluenza virus type II, parainfluenza virus type III, Leptospira spp., Campylobacter spp., Staphylococcus spp., Streptococcus spp., Mycoplasma spp., Klebsiella spp., Salmonella spp., rotavirus, coronavirus, rabies, Pasteurella spp., Clostridium spp., Tetanus toxoid, *E. coli*, and Neospora spp.

44. A combination vaccine for protecting a member of a mammalian species against mastitis and one or more diseases or pathological conditions that can afflict the mammal, which combination vaccine comprises an immunologically effective amount of a first component comprising a polynucleotide molecule comprising a nucleotide sequence encoding: (a) a peptide fragment comprising a sub-sequence of amino acids from SEQ ID NO:2 or SEQ ID NO:4 selected from the group consisting of amino acids at positions 28 to 286 and 28 to 170; or (b) a fusion protein comprising a fusion partner fused to the peptide fragment of (a); which polynucleotide molecule, or peptide fragment or fusion protein encoded thereby, is capable of inducing a protective response against mastitis in the mammal; an immunologically effective amount of a second component comprising an antigen different from the antigen in the first component and capable of inducing a protective response against a disease or pathological condition that can afflict the mammal; and a veterinarily acceptable carrier.

45. The combination vaccine of claim 44, comprising a host cell associated as a pathogen with a disease or pathological condition other than mastitis caused by *S. uberis*, which disease or pathological condition can afflict the mammal, which host cell is transformed with the polynucleotide molecule comprising the nucleotide sequence encoding the peptide fragment or fusion protein; which polynucleotide molecule is expressed in the host cell to produce the peptide fragment or fusion protein, and wherein the host cell is capable of inducing a protective immune response against the disease or pathological condition other than mastitis caused by *S. uberis*.

46. The combination vaccine of claim 45, wherein the host cell is selected from the group consisting of Leptospira spp., Campylobacter spp., Staphylococcus spp., Streptococcus spp., Mycoplasma spp., Klebsiella spp., Salmonella spp., Pasteurella spp., Clostridium spp., *E. coli*, and Neospora spp.

47. The combination vaccine of claim 44, wherein the antigen of the second component of the combination vaccine is capable of inducing a protective response in the mammal against a disease, condition, or pathogen selected from the group consisting of mastitis, bovine herpes virus, bovine respiratory syncitial virus, bovine viral diarrhea virus, parainfluenza virus type I, parainfluenza virus type II, parainfluenza virus type III, Leptospira spp., Campylobacter spp., Staphylococcus spp., Streptococcus spp., Mycoplasma spp., Klebsiella spp., Salmonella spp., rotavirus, coronavirus, rabies, Pasteurella spp., Clostridium spp., Tetanus toxoid, *E. coli*, and Neospora spp.

48. A method for determining whether an animal is infected with *Streptococcus uberis*, comprising analyzing a tissue or fluid sample from the animal for the presence of a polynucleotide molecule that encodes a protein comprising the amino acid sequence from amino acid position 26 to amino acid position 286 of SEQ ID NO:2 or SEQ ID NO:4.

49. The isolated polynucleotide molecule of claim 8, wherein the peptide fragment consists of a sub-sequence of amino acids from SEQ ID NO:2 or SEQ ID NO:4 selected from the group consisting of amino acids at positions 28 to 286 and 28 to 170.

50. The isolated polynucleotide molecule of claim 14, wherein the peptide fragment consists of a sub-sequence of amino acids from SEQ ID NO:2 or SEQ ID NO:4 selected from the group consisting of amino acids at positions 28 to 286 and 28 to 170.

51. The recombinant expression vector of claim 23, wherein the peptide fragment consists of a sub-sequence of amino acids from SEQ ID NO:2 or SEQ ID NO:4 selected from the group consisting of amino acids at positions 28 to 286 and 28 to 170.

52. The vaccine of claim 36, wherein the peptide fragment consists of a sub-sequence of amino acids from SEQ ID NO:2 or SEQ ID NO:4 selected from the group consisting of amino acids at positions 28 to 286 and 28 to 170.

53. The combination vaccine of claim 44, wherein the peptide fragment consists of a sub-sequence of amino acids from SEQ ID NO:2 or SEQ ID NO:4 selected from the group consisting of amino acids at positions 28 to 286 and 28 to 170.

54. The method of claim 48, wherein the analysis is conducted by carrying out an amplification technique that specifically detects the presence of a polynucleotide molecule comprising the nucleotide sequence from nucleotide position 195 to nucleotide position 447 of SEQ ID NO:1, or from nucleotide position 196 to nucleotide position 448 of SEQ ID NO:3.

* * * * *

SEQUENCE LISTING (1) GENERAL INFORMATION:

(iii) NUMBER OF SEQUENCES: 28

(2) INFORMATION FOR SEQ ID NO:1:

(i) SEQUENCE CHARACTERISTICS:
      (A) LENGTH: 1180 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 120..980

(xi) SEQUENCE DESCRIPTION: SEQ ID NO:1:

```
GGGCTGCAGA TCCGTTAAAA AATGACATTA ATATCTACTT CAATTTGTTC TAAAATGAAA        60

TTATATTCAC TGCTGTTACA TAACTTTGTG ATTATTTAGG ATAAAATAAG GGAGATTTT        119

ATG AAA AAA TGG TTT TTA ATA TTA ATG CTT TTG GGA ATA TTT GGT TGT        167
Met Lys Lys Trp Phe Leu Ile Leu Met Leu Leu Gly Ile Phe Gly Cys
  1               5                  10                  15

GCT ACT CAA CCA TCA AAG GTT GCA GCA ATA ACC GGT TAT GAT TCC GAC        215
```

```
Ala Thr Gln Pro Ser Lys Val Ala Ala Ile Thr Gly Tyr Asp Ser Asp
             20                  25                  30

TAC TAC GCT AGA TAT ATT GAT CCC GAT GAA AAT AAA ATA ACA TTT GCC    263
Tyr Tyr Ala Arg Tyr Ile Asp Pro Asp Glu Asn Lys Ile Thr Phe Ala
         35                  40                  45

ATA AAT GTT GAT GGT TTT GTC GAA GGT AGT AAT CAA GAA ATC CTT ATT    311
Ile Asn Val Asp Gly Phe Val Glu Gly Ser Asn Gln Glu Ile Leu Ile
 50                  55                  60

AGA GGA ATT CAT CAT GTT TTA ACA GAT CAA AAC CAA AAG ATT GTT ACA    359
Arg Gly Ile His His Val Leu Thr Asp Gln Asn Gln Lys Ile Val Thr
 65                  70                  75                  80

AAG GCC GAG TTG TTA GAC GCT ATT AGA CAT CAA ATG GTT CTT CTA CAA    407
Lys Ala Glu Leu Leu Asp Ala Ile Arg His Gln Met Val Leu Leu Gln
                 85                  90                  95

TTG GAT TAT TCC TAT GAA CTA GTC GAC TTT GCG CCT GAT GCA CAA TTA    455
Leu Asp Tyr Ser Tyr Glu Leu Val Asp Phe Ala Pro Asp Ala Gln Leu
             100                 105                 110

TTA ACA CAA GAT CGA CGG CTT TTA TTT GCC AAT CAA AAT TTT GAG GAA    503
Leu Thr Gln Asp Arg Arg Leu Leu Phe Ala Asn Gln Asn Phe Glu Glu
         115                 120                 125

TCC GTA TCA CTT GAA GAT ACT ATT CAA GAA TAC CTT TTA AAA GGG CAT    551
Ser Val Ser Leu Glu Asp Thr Ile Gln Glu Tyr Leu Leu Lys Gly His
130                 135                 140

GTT ATT CTC AGA AAA CGG GTT GAA GAA CCT ATC ACT CAT CCT ACT GAG    599
Val Ile Leu Arg Lys Arg Val Glu Glu Pro Ile Thr His Pro Thr Glu
145                 150                 155                 160

ACT GCT AAT ATT GAG TAT AAA GTT CAA TTC GCG ACT AAA GAT GGG GAA    647
Thr Ala Asn Ile Glu Tyr Lys Val Gln Phe Ala Thr Lys Asp Gly Glu
             165                 170                 175

TTC CAC CCA CTA CCT ATT TTT GTA GAC TAC GGA GAA AAA CAT ATT GGA    695
Phe His Pro Leu Pro Ile Phe Val Asp Tyr Gly Glu Lys His Ile Gly
         180                 185                 190

GAA AAA TTA ACC TCT GAC GAG TTT CGA AAA ATT GCA GAA GAA AAG CTT    743
Glu Lys Leu Thr Ser Asp Glu Phe Arg Lys Ile Ala Glu Glu Lys Leu
     195                 200                 205

TTG CAA CTC TAC CCT GAC TAT ATG ATT GAT CAA AAA GAA TAT ACT ATC    791
Leu Gln Leu Tyr Pro Asp Tyr Met Ile Asp Gln Lys Glu Tyr Thr Ile
210                 215                 220

ATT AAA CAC AAT TCT CTT GGT CAA CTT CCA AGA TAT TAT TCT TAT CAA    839
Ile Lys His Asn Ser Leu Gly Gln Leu Pro Arg Tyr Tyr Ser Tyr Gln
225                 230                 235                 240

GAT CAT TTC AGC TAC GAA ATT CAA GAT AGG CAA CGT ATC ATG GCT AAG    887
Asp His Phe Ser Tyr Glu Ile Gln Asp Arg Gln Arg Ile Met Ala Lys
                 245                 250                 255

GAC CCA AAA TCC GGA AAA GAA CTC GGT GAA ACT CAA AGT ATT GAT AAT    935
Asp Pro Lys Ser Gly Lys Glu Leu Gly Glu Thr Gln Ser Ile Asp Asn
             260                 265                 270

GTT TTT GAG AAA TAC CTT ATT ACC AAA AAA AGT TAT AAA CCT TAAAGGAAGT 987
Val Phe Glu Lys Tyr Leu Ile Thr Lys Lys Ser Tyr Lys Pro
         275                 280                 285

ATCCATTAAA TTTTTCTGCA TCACTAAAAA AACACGAGCA TCACTTTCAA AGGGACGGCC   1047

TTCGTTAGTA ACGCTAGTGT TTTTATTTTA TTTTTTTCTT TAGATCAAAC AAAACAGTCA   1107

TAGCTTCCAT TGGAGTCATA TTCATGACAT CTACTTCTTT AAGTCTATTA ATGATATCTA   1167

GAGAGGAATC TCA                                                     1180
```

(2) INFORMATION FOR SEQ ID NO:2:

(i) SEQUENCE CHARACTERISTICS:

(A) LENGTH: 286 amino acids
            (B) TYPE: amino acid
            (D) TOPOLOGY: linear (ii) MOLECULE TYPE: protein (xi) SEQUENCE DESCRIPTION: SEQ ID NO:2:

Met Lys Lys Trp Phe Leu Ile Leu Met Leu Leu Gly Ile Phe Gly Cys
 1               5                  10                  15

Ala Thr Gln Pro Ser Lys Val Ala Ala Ile Thr Gly Tyr Asp Ser Asp
                20                  25                  30

Tyr Tyr Ala Arg Tyr Ile Asp Pro Asp Glu Asn Lys Ile Thr Phe Ala
            35                  40                  45

Ile Asn Val Asp Gly Phe Val Glu Gly Ser Asn Gln Glu Ile Leu Ile
    50                  55                  60

Arg Gly Ile His His Val Leu Thr Asp Gln Asn Gln Lys Ile Val Thr
65                  70                  75                  80

Lys Ala Glu Leu Leu Asp Ala Ile Arg His Gln Met Val Leu Leu Gln
                85                  90                  95

Leu Asp Tyr Ser Tyr Glu Leu Val Asp Phe Ala Pro Asp Ala Gln Leu
            100                 105                 110

Leu Thr Gln Asp Arg Arg Leu Leu Phe Ala Asn Gln Asn Phe Glu Glu
        115                 120                 125

Ser Val Ser Leu Glu Asp Thr Ile Gln Glu Tyr Leu Leu Lys Gly His
    130                 135                 140

Val Ile Leu Arg Lys Arg Val Glu Glu Pro Ile Thr His Pro Thr Glu
145                 150                 155                 160

Thr Ala Asn Ile Glu Tyr Lys Val Gln Phe Ala Thr Lys Asp Gly Glu
                165                 170                 175

Phe His Pro Leu Pro Ile Phe Val Asp Tyr Gly Glu Lys His Ile Gly
            180                 185                 190

Glu Lys Leu Thr Ser Asp Glu Phe Arg Lys Ile Ala Glu Glu Lys Leu
        195                 200                 205

Leu Gln Leu Tyr Pro Asp Tyr Met Ile Asp Gln Lys Glu Tyr Thr Ile
    210                 215                 220

Ile Lys His Asn Ser Leu Gly Gln Leu Pro Arg Tyr Tyr Ser Tyr Gln
225                 230                 235                 240

Asp His Phe Ser Tyr Glu Ile Gln Asp Arg Gln Arg Ile Met Ala Lys
                245                 250                 255

Asp Pro Lys Ser Gly Lys Glu Leu Gly Glu Thr Gln Ser Ile Asp Asn
            260                 265                 270

Val Phe Glu Lys Tyr Leu Ile Thr Lys Lys Ser Tyr Lys Pro
        275                 280                 285

(2) INFORMATION FOR SEQ ID NO:3:

(i) SEQUENCE CHARACTERISTICS:
        (A) LENGTH: 1181 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 121..981

(xi) SEQUENCE DESCRIPTION: SEQ ID NO:3:

```
GGGCTGCAGA TCCGTTAAAA AATGACATTA ATATCTACTT CAATTTGTTC TAAAATGAAA      60

TTATATTCAC TGCTGTTACA TAACTTTGTG ATTATTTAGG ATAAAATAAG GGAGATTTTT     120

ATG AAA AAA TGG TTT TTA ATA TTA ATG CTT TTG GGA ATA TTT GGT TGT      168
Met Lys Lys Trp Phe Leu Ile Leu Met Leu Leu Gly Ile Phe Gly Cys
 1           5                  10                  15

GCT ACT CAA CCA TCA AAG GTT GCA GCA ATA ACC GGT TAT GAT TCC GAC      216
Ala Thr Gln Pro Ser Lys Val Ala Ala Ile Thr Gly Tyr Asp Ser Asp
            20                  25                  30

TAC TAC GCT AGA TAT ATT GAT CCC GAT GAA AAT AAA ATA ACA TTT GCC      264
Tyr Tyr Ala Arg Tyr Ile Asp Pro Asp Glu Asn Lys Ile Thr Phe Ala
        35                  40                  45

ATA AAT GTT GAT GGT TTT GTC GAA GGT AGT AAT CAA GAA ATC CTT ATT      312
Ile Asn Val Asp Gly Phe Val Glu Gly Ser Asn Gln Glu Ile Leu Ile
50                  55                  60

AGA GGA ATT CAT CAT GTT TTA ACA AAT CAA AAC CAA AAG ATT GTT ACA      360
Arg Gly Ile His His Val Leu Thr Asn Gln Asn Gln Lys Ile Val Thr
 65                  70                  75                  80

AAG GCC GAG TTG TTA GAC GCT ATT AGA CAT CAA ATG GTT CTT CTA CAA      408
Lys Ala Glu Leu Leu Asp Ala Ile Arg His Gln Met Val Leu Leu Gln
                85                  90                  95

TTG GAT TAT TCC TAT GAA CTA GTC GAC TTT GCG CCT GAT GCA CAA TTA      456
Leu Asp Tyr Ser Tyr Glu Leu Val Asp Phe Ala Pro Asp Ala Gln Leu
            100                 105                 110

TTA ACA CGA GAT CGA CGG CTT TTA TTT GCC AAT CGA AAT TTT GAG GAA      504
Leu Thr Arg Asp Arg Arg Leu Leu Phe Ala Asn Arg Asn Phe Glu Glu
        115                 120                 125

TCC GTA TCA CTT GAA GAT ACT ATT CAA GAA TAC CTT TTA AAA GGG CAT      552
Ser Val Ser Leu Glu Asp Thr Ile Gln Glu Tyr Leu Leu Lys Gly His
130                 135                 140

GTT ATT CTC AGA AAA CGG GTT GAA GAA CCT ATC ACT CAT CCT ACT GAG      600
Val Ile Leu Arg Lys Arg Val Glu Glu Pro Ile Thr His Pro Thr Glu
145                 150                 155                 160

ACT GCT AAT ATT GAG TAT AAA GTT CAA TTC GCG ACT AAA GAT GGG GAA      648
Thr Ala Asn Ile Glu Tyr Lys Val Gln Phe Ala Thr Lys Asp Gly Glu
                165                 170                 175

TTC CAC CCA CTA CCT ATT TTT GTA GAC TAC GGA GAA AAA CAT ATT GGA      696
Phe His Pro Leu Pro Ile Phe Val Asp Tyr Gly Glu Lys His Ile Gly
            180                 185                 190

GAA AAA TTA ACC TCT GAC GAG TTT CGA AAA ATT GCA GAA GAA AAG CTT      744
Glu Lys Leu Thr Ser Asp Glu Phe Arg Lys Ile Ala Glu Glu Lys Leu
        195                 200                 205

TTG CAA CGC TAC CCT GAC TAT ATG ATT GAT CAA AAA GAA TAT ACT ATC      792
Leu Gln Arg Tyr Pro Asp Tyr Met Ile Asp Gln Lys Glu Tyr Thr Ile
210                 215                 220

ATT AAA CAC AAT TCT CTT GGT CAA CTT CCA AGA TAT TAT TCT TAT CCA      840
Ile Lys His Asn Ser Leu Gly Gln Leu Pro Arg Tyr Tyr Ser Tyr Pro
225                 230                 235                 240

GAT GAT TTC AGC TAC GAA ATT CAA GAT AGG CAA CGT ATC ATG GCT AAG      888
Asp Asp Phe Ser Tyr Glu Ile Gln Asp Arg Gln Arg Ile Met Ala Lys
                245                 250                 255

GAC CCA AAG TCC GGA AAA GAA CTC GGT GAA ACT CAA AGT ATT GAT AAT      936
Asp Pro Lys Ser Gly Lys Glu Leu Gly Glu Thr Gln Ser Ile Asp Asn
            260                 265                 270

GTT TTT GAG AAA TAC CTT ATT ACC AAA AAA AGT TAT AAA CCT TAAATGAAGT   988
Val Phe Glu Lys Tyr Leu Ile Thr Lys Lys Ser Tyr Lys Pro
        275                 280                 285

ATCCATTAAA TTTTTCTGCA TCACTAAAAA AACACGAGCA TCACTTTCAA AGGGAAGGCC   1048

TTCGTTAGTA ACGCTAGTGT TTTTATTTTA TTTTTTTCTT TAAATCAAAC AAAACAGTCA   1108
```

TAGCTTCCAT TGGAGTCATA TTCATGACAT CTACTTCTTT AAGTCTATTA ATGATATCTA    1168

GAGAGGAATC TCA                                                      1181

(2) INFORMATION FOR SEQ ID NO:4:

(i) SEQUENCE CHARACTERISTICS:
        (A) LENGTH: 286 amino acids
        (B) TYPE: amino acid
        (D) TOPOLOGY: linear (ii) MOLECULE TYPE: protein (xi) SEQUENCE DESCRIPTION: SEQ ID NO:4:

Met Lys Lys Trp Phe Leu Ile Leu Met Leu Leu Gly Ile Phe Gly Cys
 1               5                  10                  15

Ala Thr Gln Pro Ser Lys Val Ala Ala Ile Thr Gly Tyr Asp Ser Asp
                20                  25                  30

Tyr Tyr Ala Arg Tyr Ile Asp Pro Asp Glu Asn Lys Ile Thr Phe Ala
                35                  40                  45

Ile Asn Val Asp Gly Phe Val Glu Gly Ser Asn Gln Glu Ile Leu Ile
 50                  55                  60

Arg Gly Ile His His Val Leu Thr Asn Gln Asn Gln Lys Ile Val Thr
 65                  70                  75                  80

Lys Ala Glu Leu Leu Asp Ala Ile Arg His Gln Met Val Leu Leu Gln
                85                  90                  95

Leu Asp Tyr Ser Tyr Glu Leu Val Asp Phe Ala Pro Asp Ala Gln Leu
                100                 105                 110

Leu Thr Arg Asp Arg Arg Leu Leu Phe Ala Asn Arg Asn Phe Glu Glu
                115                 120                 125

Ser Val Ser Leu Glu Asp Thr Ile Gln Glu Tyr Leu Leu Lys Gly His
 130                 135                 140

Val Ile Leu Arg Lys Arg Val Glu Glu Pro Ile Thr His Pro Thr Glu
 145                 150                 155                 160

Thr Ala Asn Ile Glu Tyr Lys Val Gln Phe Ala Thr Lys Asp Gly Glu
                165                 170                 175

Phe His Pro Leu Pro Ile Phe Val Asp Tyr Gly Glu Lys His Ile Gly
                180                 185                 190

Glu Lys Leu Thr Ser Asp Glu Phe Arg Lys Ile Ala Glu Glu Lys Leu
                195                 200                 205

Leu Gln Arg Tyr Pro Asp Tyr Met Ile Asp Gln Lys Glu Tyr Thr Ile
 210                 215                 220

Ile Lys His Asn Ser Leu Gly Gln Leu Pro Arg Tyr Tyr Ser Tyr Pro
 225                 230                 235                 240

Asp Asp Phe Ser Tyr Glu Ile Gln Asp Arg Gln Arg Ile Met Ala Lys
                245                 250                 255

Asp Pro Lys Ser Gly Lys Glu Leu Gly Glu Thr Gln Ser Ile Asp Asn
                260                 265                 270

Val Phe Glu Lys Tyr Leu Ile Thr Lys Lys Ser Tyr Lys Pro
                275                 280                 285

(2) INFORMATION FOR SEQ ID NO:5:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (v) FRAGMENT TYPE: internal (ix) FEATURE:
             (A) NAME/KEY: Peptide
             (B) LOCATION: 1..18
             (D) OTHER INFORMATION: /label= Xaa
                 /note= "Xaa = Pro or Gly"

(xi) SEQUENCE DESCRIPTION: SEQ ID NO:5:

Ile Thr Xaa Tyr Asp Ser Asp Tyr Tyr Ala Arg Tyr Ile Asp Pro Asp
1               5                  10                  15

Glu Asn (2) INFORMATION FOR SEQ ID NO:6:

(i) SEQUENCE CHARACTERISTICS:
             (A) LENGTH: 31 amino acids
             (B) TYPE: amino acid
             (C) STRANDEDNESS: single
             (D) TOPOLOGY: linear (ii) MOLECULE TYPE: peptide (v) FRAGMENT TYPE: internal (xi) SEQUENCE DESCRIPTION: SEQ ID NO:6:

Tyr Ile Asp Pro Asp Glu Asn Lys Ile Thr Phe Ala Ile Asn Val Asp
1               5                  10                  15

Gly Phe Val Glu Gly Ser Asn Gln Glu Ile Leu Ile Arg Gly Ile
                20                  25                  30

(2) INFORMATION FOR SEQ ID NO:7:

(i) SEQUENCE CHARACTERISTICS:
             (A) LENGTH: 12 amino acids
             (B) TYPE: amino acid
             (C) STRANDEDNESS: single
             (D) TOPOLOGY: linear (ii) MOLECULE TYPE: peptide (v) FRAGMENT TYPE: internal (xi) SEQUENCE DESCRIPTION: SEQ ID NO:7:

Ile Val Thr Lys Ala Glu Leu Leu Asp Ala Ile Arg
1               5                  10

(2) INFORMATION FOR SEQ ID NO:8:

(i) SEQUENCE CHARACTERISTICS:
             (A) LENGTH: 16 amino acids
             (B) TYPE: amino acid
             (C) STRANDEDNESS: single
             (D) TOPOLOGY: linear (ii) MOLECULE TYPE: peptide (v) FRAGMENT TYPE: internal (ix) FEATURE:
             (A) NAME/KEY: Peptide
             (B) LOCATION: 1..16
             (D) OTHER INFORMATION: /label= Xaa
                 /note= "Xaa = Unknown"

(xi) SEQUENCE DESCRIPTION: SEQ ID NO:8:

Asp Gly Glu Phe His Pro Leu Pro Ile Phe Val Xaa Tyr Xaa Glu Lys

```
 1               5                  10                 15
```

(2) INFORMATION FOR SEQ ID NO:9:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:9:

```
Leu Leu Gln Leu Tyr Pro Asp Tyr Met Ile Asp Gln Lys
1               5                  10
```

(2) INFORMATION FOR SEQ ID NO:10:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:10:

```
Leu Leu Gln Leu Tyr Pro Asp Tyr Met Ile Asp Gln Lys Glu Tyr Thr
1               5                  10                 15

Ile Ile Lys
```

(2) INFORMATION FOR SEQ ID NO:11:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:11:

```
Tyr Tyr Ser Tyr Gln Asp His Phe Ser Tyr Glu Ile Gln Asp Arg
1               5                  10                 15
```

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:12:

```
Tyr Leu Ile Thr Lys
1               5
```

(2) INFORMATION FOR SEQ ID NO:13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

ATCATATAGT CAGGGTAGAG                                                        20

(2) INFORMATION FOR SEQ ID NO:14:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:14:

CGGGTACCGW TATATTGATC CWGATGARAA                                             30

(2) INFORMATION FOR SEQ ID NO:15:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:15:

GGGGATCCTT TTGATCAATW GGATAATCWG GATA                                        34

(2) INFORMATION FOR SEQ ID NO:16:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:16:

GGGGATCCTT YTGRTCRATW GGRTARTCWG GRTA                                        34

(2) INFORMATION FOR SEQ ID NO:17:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:17:

GTTACAAAGG CCGAGTTGTT AGAC                                                   24

(2) INFORMATION FOR SEQ ID NO:18:

(i) SEQUENCE CHARACTERISTICS:
            (A) LENGTH: 25 base pairs
            (B) TYPE: nucleic acid
            (C) STRANDEDNESS: single (D) TOPOLOGY: linear (ii) MOLECULE TYPE: DNA (genomic)

(xi) SEQUENCE DESCRIPTION: SEQ ID NO:18:

GATTGGCAAA TAAAAGCCGT CGATC                                              25

(2) INFORMATION FOR SEQ ID NO:19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CTTCAAGTGA TACGGATTCC TC                                                 22

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GGGGAATTCC ACCCACTACC                                                    20

(2) INFORMATION FOR SEQ ID NO:21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GACGAGTTTC GAAAAATTGC AGAAG                                              25

(2) INFORMATION FOR SEQ ID NO:22:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GGGCTGCAGT CATATGAAAA AATGGTTTTT AATATTAATG CTTTTGGG                     48

(2) INFORMATION FOR SEQ ID NO:23:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GGGCTGCAGT CATATGATAA CCGGTTATGA TTCCGACTAC TACG					44

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GAGATTCCTC TCTAGATATC A					21

(2) INFORMATION FOR SEQ ID NO:25:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GGGCTGCAGA TCCGTTAAAA AATGACATTA ATAT					34

(2) INFORMATION FOR SEQ ID NO:26:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus uberis (xi) SEQUENCE DESCRIPTION: SEQ ID NO:26:

GCGGCTCGAG ACCGGTTATG ATTCCGACTA C					31

(2) INFORMATION FOR SEQ ID NO:27:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus uberis (xi) SEQUENCE DESCRIPTION: SEQ ID NO:27:

GTTGCGGCCG CGGATACTTC ATTTAAGGTT TAT					33

(2) INFORMATION FOR SEQ ID NO:28:

```
    (i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
         (A) ORGANISM: Streptococcus uberis (xi) SEQUENCE DESCRIPTION: SEQ ID NO:28:

Lys Arg Val Glu Glu Pro Ile Thr His Pro
1               5                   10
```